(12) United States Patent
Leow et al.

(10) Patent No.: US 12,291,794 B2
(45) Date of Patent: *May 6, 2025

(54) ELECTROSYNTHESIS OF OXIRANES

(71) Applicant: THE GOVERNING COUNCIL OF THE UNIVERSITY OF TORONTO, Toronto (CA)

(72) Inventors: Wan Ru Leow, Singapore (SG); Yanwei Lum, Singapore (SG); Edward Sargent, Toronto (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/915,209

(22) PCT Filed: Mar. 18, 2021

(86) PCT No.: PCT/CA2021/050361
§ 371 (c)(1),
(2) Date: Sep. 28, 2022

(87) PCT Pub. No.: WO2021/195746
PCT Pub. Date: Oct. 7, 2021

(65) Prior Publication Data
US 2023/0146508 A1     May 11, 2023

Related U.S. Application Data

(60) Provisional application No. 63/002,653, filed on Mar. 31, 2020.

(51) Int. Cl.
*B01J 21/06*     (2006.01)
*B01J 23/46*     (2006.01)
(Continued)

(52) U.S. Cl.
CPC .............. *C25B 3/07* (2021.01); *C25B 3/05* (2021.01); *C25B 11/031* (2021.01);
(Continued)

(58) Field of Classification Search
CPC ......... B01J 21/063; B01J 23/468; C25B 3/05; C25B 3/07; C25B 11/031; C25B 11/052; C25B 11/063; C25B 11/075; C25B 15/081
(Continued)

(56) References Cited

U.S. PATENT DOCUMENTS 3,288,692 A    11/1966   Leduc
9,561,497 B2*   2/2017   Kumta ................. H01M 4/881
(Continued)

FOREIGN PATENT DOCUMENTS

AU     2017209876     7/2017

OTHER PUBLICATIONS

Leow, et al., Chloride-mediated selective electrosynthesis of ethylene and propylene oxides at high current density:, Science, 368; 1228-1233. (Year: 2020).*

(Continued)

*Primary Examiner* — Cam N. Nguyen
(74) *Attorney, Agent, or Firm* — Stradley Ronon Stevens & Young, LLP

(57) ABSTRACT

Electrosynthesis of oxirane can include contacting a halide electrolyte with an anode and cathode respectively located in anodic and cathodic compartments; supplying olefin reactants into the electrolyte in the anodic compartment, such that the anode generates ethylene chlorohydrin; withdrawing a loaded anodic solution comprising ethylene halohydrin from the anodic compartment, and a loaded cathodic solution comprising OH⁻ ions from the cathodic compartment; and mixing the loaded anodic solution with the loaded (Continued)

cathodic solution under conditions to react ethylene halohydrin with OH— to produce oxirane. The electrocatalyst can include iridium oxide on a titanium substrate, with the iridium oxide provided as nanoparticles on a titanium mesh, and the electrolyte can be aqueous KCl. The electrocatalyst can define an extended heterogenous:homogenous interface with halide ions acting as a reservoir for positive charges, thereby storing and redistributing positive charges to promote selective generation of ethylene halohydrins.

19 Claims, 24 Drawing Sheets

(51) Int. Cl.
| | |
|---|---|
| C25B 3/05 | (2021.01) |
| C25B 3/07 | (2021.01) |
| C25B 11/031 | (2021.01) |
| C25B 11/052 | (2021.01) |
| C25B 11/063 | (2021.01) |
| C25B 11/075 | (2021.01) |
| C25B 15/08 | (2006.01) |

(52) U.S. Cl.
CPC .......... *C25B 11/052* (2021.01); *C25B 11/063* (2021.01); *C25B 11/075* (2021.01); *C25B 15/081* (2021.01)

(58) Field of Classification Search
USPC .......................................................... 502/300
See application file for complete search history.

(56) References Cited

U.S. PATENT DOCUMENTS

| | | | |
|---|---|---|---|
| 2007/0034505 A1* | 2/2007 | Ikematsu | C25B 1/13 427/372.2 |
| 2017/0233879 A1* | 8/2017 | Kumta | C25B 9/73 502/226 |
| 2019/0032228 A1 | 1/2019 | Krause et al. | |
| 2021/0340682 A1* | 11/2021 | Lee | C25B 11/093 |

OTHER PUBLICATIONS

International Search Report and Writen Opinion issued May 27, 2021 in International Application No. PCT/CA2021/050361.
Use of Energy Explained Energy Use in Industry, U.S. Energy Information Administration, https://eia.gov/energyexplained/us-of-energy/industry.php, obtained Mar. 31, 2023.
Chu et al. The Path towards sustainable energy, Nature Materials, vol. 16, pp. 16-22, Jan. 2017.
Seh et al., Combining theory and experiment in electrocatalysis: Insights into materials design, Science, 355, 146, 13 pages, Jan. 2017.
Zheng et al., Strategies to reduce the global carbon footprint of plastics, Nature Climate Change, vol. 9, pp. 374-378, May 2019.
Luna et al., What would it take for renewably powered electrosynthesis to displace petrochemical processes?, Science, 364, 350, 11 pages, Apr. 26, 2019.
Jouny et al., General Techno-Economic Analysis of Co2 Electrolysis Systems, Industrial & Engineering Chemistry Research, 57, pp. 2165-2177, 2018.
Xia et al., Direct electrosynthesis of pure aqueous H2O2 solutions up to 20% by weight using a solid electrolyte, Science, 366, pp. 226-231, Oct. 11, 2019.
Service, Renewable Bonds With solar and wind booming the chemical industry dabbles with forgoing petroleum as its feedstock, Science, vol. 365, Issue 6459, Sep. 20, 2019.
Rebsdat et al., Ethylene Oxide, Ullmann's Encyclopedia of Industrial Chemistry, vol. 13, pp. 547-572, 2012.
Ethylene Oxide, Iarc Monographs—100F, pp. 379-400.
Wismann et al., Electrified methane reforming: A compact approach to greener industrial hydrogen production, Science, 364, pp. 756-759, May 24, 2019.
Market Analytics: Propylene Oxide 2020, Nexant Market & Profitability, 2 pages.
Van Geem et al., Making chemicals with electricity, Science, vol. 364, Issue 6442, pp. 734-735, May 24, 2019.
Dudley, Renewable Energy Costs Take Another Tumble, Making Fossil Fuels Look More Expensive Than Ever, https://www.forbes.com/sites/dominicdudley/2019/05/29/renewable-energy-cost-tumble/?sh=7eebeaa5e8ce, May 29, 2019.
Cha et al., Combined biomass valorization and hydrogen production in a photoelectrochemical cell, Nature Chemistry, vol. 7, pp. 328-333, Apr. 2015.
Jiang et al., Integrating Electrocatalytic 5-Hydroxymethylfurfural Oxidation and Hydrogen Production via Co-P-Derived Electrocatalysts, ACS Energy Letters, 1, pp. 386-390, 2016.
You et al., Simultaneous H2 Generation and Biomass Upgrading in Water by an Effcient Noble-Metal-Free Bifunctional Electrocatlyst, Angewandte Chemie, 55, pp. 9913-9917, 2016.
Zheng et al., Hierarchical Porous NC@Cuco Nitride Nanosheet Networks: Highly Efficient Bifunctional Electrocatalyst for Overall Water Splitting and Selective Electrooxidation of Benzyl Alcohol, Advanced Functional Materials, 27, 12 pages, 2017.
Li et al., Electrolytic CO2 Reduction in Tandem with Oxidative Organic Chemistry, ACS Central Science, 3, pp. 778-783, 2017.
Liu et al., Selective photoelectrochemical oxidation of glycerol to high value-added dihydroxyacetone, Nature Communications, 1-8 pages, 2019.
Kwon et al., Highly Selective Electro-Oxidation of Glycerol to Dihydroxyacetone on Platinum in the Presence of Bismuth, ACS Catalysis, 2, pp. 759-764, 2012.
Dai et al., Eletrochemical production of lactic acid from glycerol oxidation catalyzed by AuPt nanoparticles, Journal of Catalysis, 356, pp. 14-21, 2017.
Winiwarter et al., Towards an atomistic understanding of electocatalytic partial hydrocarbon oxidation: propene on palladium, Energy & Environmental Science, 12, pp. 1055-1067, 2019.
Huang et al., Boosting Hydrogen Production by Anodic Oxidation of Primary Amines over a NiSe Nanorod Electrode, Angew Chem, Int. Ed. 57, pp. 13163-13166, 2018.
Huang et al., Integrating Hydrogen Production with Aqueous Selective Semi-Dehydrogenation of Tetrahydroisoquinolines over a Ni2P Bifunctional Electrode, Angew Chem Int. Ed. 58, pp. 12014-12017, 2019.
Lum et al., Tuning OH Binding energy enables selective electrochemical oxidation of ethylene to ethylene glycol, Nature Catalysis, vol. 3, pp. 14-22, Jan. 2020.
Rafiee et al., Electrocatalytic Alcohol Oxidation with TEMPO and Bicyclic Nitroxyl Derivatives: Driving Force Trumps Steric Effects, Journal of the American Chemical Society, 137, pp. 14751-14757, 2015.
Horn et al., Scalable and sustainable electrochemical allylic C—H oxidation, Nature, vol. 533, pp. 77-81, May 5, 2016.
Rafiee et al., N-Hydroxphthalimide-Mediated Electrochemical Lodination of Methylarenes and Comparison to Electron-Transfer-Initated C—H Functionalization, Journal of the American Chemical Society, 140, pp. 22-25, 2018.
Eigen et al., The Kinetics of Halogen Hydrolysis, The Max-Planck-Institut for Phsikalische Chemie, Goettingen, Germany, pp. 1355-1361, Apr. 20, 1962.
McCabe et al., The Kinetics of Reaction between the Ethylene Halohydrins and Hydroxyl Ion in Water and Mixed Solvents, The Department of Chemistry, Carnegie Institute of Technology, vol. 70, pp. 4031-4034, Dec. 1948.
Luc et al., An Ir-based anode for a practical CO2 electrolyzer, Catalysis Today, 288, pp. 79-84, 2017.
Sherbo et al., Complete electron economy by pairing electrolysis with hydrogenation, Nature Catalysis, vol. 1, pp. 501-507, Jul. 2018.

* cited by examiner

ELECTROSYNTHESIS OF OXIRANES

TECHNICAL FIELD

The technical field generally relates to the synthesis of oxiranes, and more particularly to techniques for the electrocatalytic conversion of olefins into oxiranes.

BACKGROUND

Oxirane is used in the manufacture of plastics, detergents, thickeners and solvents, and is among the world's top fifteen most produced chemicals at about 20 million metric tons per annum. At present, it is manufactured via the thermocatalytic partial oxidation of ethylene at high temperature and pressure, e.g., 200-300° C. and 1-3 MPa, generating 1.6 tons of $CO_2$ per ton oxirane produced. There are a number of drawbacks and challenges with respect to the production of oxiranes.

SUMMARY

Various implementations, features and aspects of the technology are described herein, including in the claims, figures and following description.

For example, in some implementations there is provided an electrocatalyst for selective anodic oxidation of an olefin reactant to produce ethylene chlorohydrin in a halide ion based electrolyte, the electrocatalyst comprising iridium oxide on a titanium substrate.

The iridium oxide can be provided as particles, such as nanoparticles, on the titanium substrate. The titanium mesh can include a network of filaments defining openings, and the iridium oxide can be deposited on the filaments and also forms an iridium oxide web extending across the openings. The halide ion can include Cl and the halide ion based electrolyte can be an aqueous KCl electrolyte.

In some implementations, there is provided an electrochemical process for producing oxirane from olefin reactants, comprising: contacting a halide based electrolyte with an anode and a cathode respectively located in an anodic compartment and a cathodic compartment; supplying olefin reactants into the electrolyte in the anodic compartment, such that the anode generates ethylene chlorohydrin; withdrawing a loaded anodic solution comprising ethylene halohydrin from the anodic compartment, and a loaded cathodic solution comprising OH-ions from the cathodic compartment; and mixing at least a portion of the loaded anodic solution with at least a portion of the loaded cathodic solution under conditions to react ethylene halohydrin with OH— to produce oxirane.

The olefin reactants can include ethylene and/or propylene. The halide based electrolyte can be Cl based and the ethylene halohydrin and include ethylene chlorohydrin. The halide based electrolyte can be provided at a concentration of about 1.5 to 2.5 M or about 1.8 to 2.2 M. The anode can include an electrocatalyst comprising a metal oxide catalyst provided on a metal substrate, and the metal oxide catalyst can include iridium, such as iridium oxide, which can be provided in particulate form on a metal mesh that can be made of titanium. The electrocatalyst can be fabricated by etching the metal substrate followed by coating the etched metal substrate in a coating solution comprising a dihydrate of the metal oxide catalyst.

In some implementations, there is provided an electrochemical process for producing oxirane from olefin reactants, comprising: contacting a halide based electrolyte with an anode and a cathode respectively located in an anodic compartment and a cathodic compartment; supplying olefin reactants into the electrolyte in the anodic compartment, such that the anode generates ethylene halohydrin; withdrawing a loaded anodic solution comprising ethylene halohydrin from the anodic compartment; contacting at least a portion of the loaded anodic solution with a basic solution comprising OH-ions under conditions to react ethylene halohydrin with OH— to produce oxirane.

In some implementations, there is provided an electrochemical system for producing oxirane from olefin reactants, comprising an electrochemical flow cell comprising an anodic compartment having an anode provided therein, an electrolyte inlet for receiving a halide based electrolyte, a gas inlet for supplying olefin reactants to electrocatalytically convert the olefin and halide into ethylene halohydrin, and an outlet for expelling a solution comprising the ethylene halohydrin; a cathodic compartment having a cathode provided therein, an electrolyte inlet for receiving a halide based electrolyte, a hydrogen outlet, and an outlet for expelling a basic solution comprising OH-ions; and an ion exchange membrane between the anodic and cathodic compartments. The system also includes a mixing chamber configured to receive at least a portion of the solution comprising the ethylene halohydrin and the basic solution comprising $OH^-$ ions, or a mixture thereof, and to provide conditions to react ethylene halohydrin with OH— to produce oxirane.

In some implementations, there is provided an electrochemical process for producing an organic product from olefin reactants, comprising: contacting a halide based electrolyte with an anode and a cathode respectively located in an anodic compartment and a cathodic compartment; supplying olefin reactants into the electrolyte in the anodic compartment, such that the olefin reactants contact the anode; wherein the anode comprises an electrocatalyst that defines an extended heterogenous:homogenous interface with halide ions acting as a reservoir for positive charges, thereby storing and redistributing positive charges to promote selective generation of halohydrins; and converting the halohydrins into the organic product. The halohydrins can include ethylene halohydrins, and the organic product can include or be oxiranes. The converting can include mixing at least a portion of a loaded anodic solution withdrawn from the anodic compartment, and at least a portion of a loaded cathodic solution withdrawn from the cathodic compartment.

In some implementations, there is provided an electrochemical process for producing oxiranes from olefin reactants, comprising contacting a halide based electrolyte with an anode and a cathode respectively located in an anodic compartment and a cathodic compartment; supplying olefin reactants into the electrolyte in the anodic compartment, such that the olefin reactants contact the anode; wherein the anode comprises an electrocatalyst that defines an extended heterogenous:homogenous interface with halide ions acting as a reservoir for positive charges, thereby storing and redistributing positive charges to promote selective generation of ethylene halohydrins; and converting the ethylene halohydrins into oxiranes.

The techniques described above can also be combined with one or more features as described or claimed herein.

BRIEF DESCRIPTION OF DRAWINGS

The Figures describe various aspects and information regarding the technology.

DETAILED DESCRIPTION

Figure 1A:
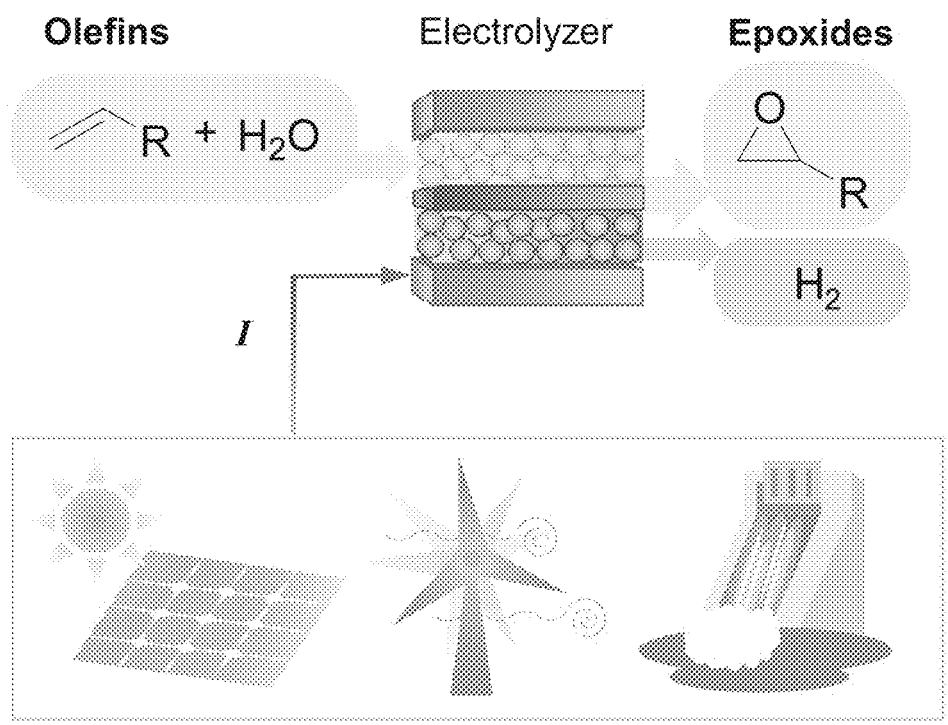
FIG. 1. Electrosynthesis of ethylene oxide using renewable energy. (A) Schematic illustrating the proposed electrochemical system. (B) Sensitivity analysis of the plant-gate levelized cost per ton of ethylene oxide (EO) produced. (C) Techno-economic analysis (TEA) showing plant-gate levelized cost as a function of energy efficiency and renewable energy cost. (D) Reported current densities and Faradaic efficiencies for other anodic partial oxidation reactions in the literature (blue squares, left of graph, references 16-28). Data for the system demonstrated in this work are shown for comparison (red squares, right of graph) (E) Breakdown of costs at current densities of 50 and 300 mA/cm$^2$, as calculated from TEA.

The present description relates to the selective electrosynthesis of oxiranes, which can be done at relatively high current density facilitated by an extended heterogeneous: homogeneous interface. In some implementations, oxirane is produced using a method that includes selective anodic oxidation under high current densities without uncontrolled oxidation by utilizing Cl$^-$ as a reservoir for positive charges the from anode to create an extended heterogeneous:homogeneous interface. In one example, the electrochemical system can include a flow-cell with a KCl based electrolyte in which ethylene is continuously sparged into the anolyte, with iridium oxide nanoparticles on titanium mesh as the working electrode (anode), and Ni foam as the counter electrode (cathode).

More broadly, an electrochemical process for producing oxirane from olefin reactants can include contacting a halide based electrolyte with an anode and a cathode respectively located in an anodic compartment and a cathodic compartment; supplying olefin reactants into the electrolyte in the anodic compartment, such that the anode electrocatalytically produces ethylene halohydrin; withdrawing a loaded anodic solution comprising ethylene halohydrin from the anodic compartment; and contacting at least a portion of the loaded anodic solution with a basic solution comprising OH-ions under conditions to react ethylene halohydrin with OH— to produce oxirane. Preferably, the basic solution comprising OH-ions is obtained from the cathodic compartment as the catholyte.

The anode can comprise an electrocatalyst for selective anodic oxidation of an olefin reactant, such as ethylene or propylene, to produce ethylene halohydrin in a halide ion based electrolyte, the electrocatalyst comprising a catalyst metal oxide on a metal substrate. The catalyst metal oxide can comprise iridium oxide and the metal substrate can comprise titanium.

In some implementations, the process enables selective anodic oxidation under high current densities without uncontrolled oxidation by utilizing $Cl^-$ as a reservoir for positive charges from the anode to create an extended heterogeneous:homogeneous interface. The olefin oxidation experiments were conducted in a flow-cell configuration consisting of 2.0 M KCl electrolyte, the iridium oxide nanoparticles on titanium mesh anode catalyst, ion exchange membrane and cathode (e.g., Ni foam). These are positioned and clamped together with spacers to enable the introduction of liquid electrolyte into the anodic and cathodic chambers. The electrolyte is circulated through the cell during which ethylene or propylene gas is continuously sparged into the anolyte at a constant flow rate. The catholyte and anolyte output streams are merged post electrolysis, oxirane can be generated from the reaction between ethylene chlorohydrin and $OH^-$. Other concentrations of the electrolyte, as well as other electrolytes comprising the halide ions $Cl^-$ and $Br^-$ can be used as well, but it was found that 2.0 M KCl provides the highest energy efficiency.

The iridium oxide nanoparticles on titanium mesh anode was fabricated by etching the titanium mesh in boiling 6 M HCl for 40 min, followed by dip-coating in a solution comprised of 2 mL HCl, 18 mL isopropanol, and 60 mg iridium (IV) oxide dihydrate. The resultant catalyst was dried in a preheated oven at 100° C. for 10 min and calcined in air at 500° C. for 10 min. The procedure was repeated 10 times to achieve an $IrO_2$ loading of ~1 $mg/cm^2$.

Thus, in some implementations, an electrochemical route for the production of oxirane at 1 $A/cm^2$ current densities was developed.

Chemicals manufacturing consumes large amounts of energy and is responsible for 15% of global carbon emissions. Electrochemical systems that produce the desired chemicals using renewable electricity offer a route to decarbonization of the chemicals sector. Oxirane is among the world's top 15 most produced chemicals at ~20 million tons yearly due to its importance in the plastics industry, notably in the manufacture of polyesters and polyethylene terephthalates (PET). If one could develop the renewable electricity powered electrosynthesis of oxirane under ambient conditions, the associated carbon emissions could be reduced. This work first utilized techno-economic analysis to determine conditions that could enable the profitable synthesis of a renewable-energy-powered anodic partial oxidation of ethylene and propylene to oxirane and methyl oxirane, respectively. This work then utilized an extended heterogeneous:homogeneous interface, using $Cl^-$ as a reservoir for positive charges from an iridium oxide nanoparticles on titanium mesh anode, to facilitate the partial anodic oxidation of ethylene to oxirane at current densities of 1 $A/cm^2$ and Faradaic efficiencies of ~70%. This work ran the system at 300 $mA/cm^2$ for 100 h and maintained a 71(±1) % Faradaic efficiency throughout. This work also achieved a Faradaic efficiency of 45% to oxirane in an integrated system using ethylene generated from a $CO_2$-to-ethylene membrane electrode assembly.

The electrosynthesis of oxirane involves the partial oxidation of ethylene, an anodic reaction. Reactions of this nature at high current density and Faradaic efficiency are hampered by two challenges. Firstly, the large positive potentials applied mean that uncontrolled over-oxidation often occurs, generating undesired byproducts such as $CO_2$. Currently, reported anodic upgrading reactions such as the oxidation of 5-hydroxymethylfurfural, alcohol and glycerol, are conducted at low current densities, since at these low current densities, high Faradaic efficiencies toward the target product have been obtained. However, the production of industrially-relevant quantities of the product at such low current densities would require unreasonably high electrolyzer surface areas, leading to high capital costs per unit of productivity. Secondly, if the reactant has limited solubility in the aqueous electrolyte (in this case, ethylene), the system quickly becomes mass-transport-limited, resulting in poor Faradaic efficiency at high current density.

The anodic electrosynthesis of olefins such as ethylene and propylene has been reported using anodes based on palladium dendritic nanotrees, achieving a Faradaic efficiency of 80% at current density of 7.1 $mA/cm^2$. This method only occurs under low current density of 7.1 $mA/cm^2$, which is two orders below industrially relevant current densities at 300-100 $mA/cm^2$. Operating at such high current densities would result in the dissolution of the Pd anode. As previously mentioned, the production of industrially-relevant quantities of the product at such low current densities would require unreasonably high electrolyzer surface areas, leading to high capital costs per unit of productivity. As renewable electricity is much more expensive than electricity derived from fossil fuels, the energy efficiency of the reaction needs to be high to ensure profitability by keeping the total electricity costs low.

Implementations described herein overcome at least some of the drawback of other techniques. For example, this work utilized $Cl^-$ or another halide as a reservoir for positive charges from the anode to create an extended heterogeneous:homogeneous interface. For instance, $Cl^-$ stores and redistributes positive charges to ethylene, thereby buffering it from uncontrolled oxidation and facilitating ethylene oxide production. Thus, this work was able to achieve high Faradaic efficiencies of ~70% under high current densities of 300-1000 $mA/cm^2$.

In terms of examples that were assessed, this was realized in a flow-cell setup with 2.0 M KCl electrolyte, in which ethylene was continuously sparged into the anolyte, with iridium oxide nanoparticles on titanium mesh as the working electrode (anode), Ni foam as the counter electrode (cathode). The final step involves addition of alkali ($OH^-$), which then reacts with ethylene chlorohydrin to yield the desired ethylene oxide and regenerate $Cl^-$: the hydrogen evolution reaction at the cathode during electrolysis generates the OH-needed to do this. This means that by merging the catholyte and anolyte output streams post electrolysis, oxirane can be generated from the reaction between ethylene chlorohydrin and $OH^-$.

In addition, this work developed an anode (iridium oxide nanoparticles on titanium mesh) and reaction conditions to enable this reaction to remain profitable even at the upper bound of renewable electricity costs. This work obtained a high energy efficiency of 31% under current density 300 $mA/cm^2$, which is key to enabling profitability by reducing the high electricity costs associated with renewable energy use. This anode also enabled us to maintain a stable applied potential of 2.86(±0.02) V and Faradaic efficiency averaging 71(±0.6) % for 100 hours continuously.

The electrocatalytic techniques described herein for producing oxiranes include features such as providing an extended heterogeneous:homogeneous interface for the electrocatalytic reactions (e.g., conversion of olefins into ethylene halohydrins in the anodic compartment), providing a halide ion positive charge reservoir proximate to the electrocatalyst of the anode, and/or the development of an electrocatalyst material for use in the anodic compartment and having certain chemical, structural and functional features (e.g., iridium oxide nanoparticles on a titanium mesh). The development of an extended heterogeneous:homogeneous interface is beneficial as it facilitates storing and redistributing positive charges to an organic molecule, thereby buffering it from uncontrolled oxidation and facilitating highly selective product generation. This facilitates anodic electrosynthesis at relatively high current densities, which in turn allow for industrially-relevant production rates without incurring unreasonably high capital costs. Another aspect is the anode based on iridium nanoparticles on titanium mesh, which facilitated this reaction to remain profitable even at the upper bound of renewable electricity costs. This is relevant in terms of providing industries with the incentive to decarbonize by making the switch from the conventional thermal ethylene oxidation process to an electrochemical one. This anode material was also able to maintain a stable applied potential of 2.86(±0.02) V and Faradaic efficiency averaging 71(±0.6) % for 100 hours continuously.

The following section provides additional background, information and experimentation regarding the technology and notably example implementations regarding the selective electrosynthesis of ethylene oxide at high current density enabled by an extended heterogeneous:homogeneous interface.

Chemicals manufacturing consumes large amounts of energy and is responsible for 15% of global carbon emissions. Electrochemical systems that produce the desired chemicals using renewable electricity offer a route to decarbonization of the chemicals sector. Ethylene oxide is among the world's top 15 most produced chemicals at ~20 million tons yearly due to its importance in the plastics industry, notably in the manufacture of polyesters and polyethylene terephthalates (PET). Here, this work utilized an extended heterogeneous:homogeneous interface, using $Cl^-$ as a reservoir for positive charges from the anode, to facilitate the partial anodic oxidation of ethylene to ethylene oxide at current densities of 1 $A/cm^2$ and Faradaic efficiencies of ~70%. This work ran the system at 300 $mA/cm^2$ for 100 h and maintained a 71(±1) % Faradaic efficiency throughout.

In the United States, chemical manufacture accounts for 28% of total industrial energy demand (1). At present, this demand is largely met by the consumption of fossil fuels, resulting in significant $CO_2$ emissions (2, 3): a recent report showed that the plastics industry alone releases 1.8 billion metric tons of $CO_2$ per year; and that replacing fossil fuels-based production methods with ones powered using renewable energy offers a route to reduce net greenhouse gas emissions associated with plastics manufacture (4).

One attractive strategy involves developing electrochemical systems that produce the necessary raw materials using renewable electricity (5-8). Ethylene oxide is used in the manufacture of plastics, detergents, thickeners and solvents (9) and among the world's top 15 most produced chemicals at ~20 million metric tons per annum (10, 11). At present, it is manufactured via the thermocatalytic partial oxidation of ethylene at high temperature and pressure (200-300° C. and 1-3 MPa), generating 1.6 tons of $CO_2$ per ton ethylene oxide produced (12). If one could develop the renewable electricity powered electrosynthesis of ethylene oxide under ambient conditions, the associated carbon emissions could be reduced (FIG. 1A) (13, 14).

Figure 5:
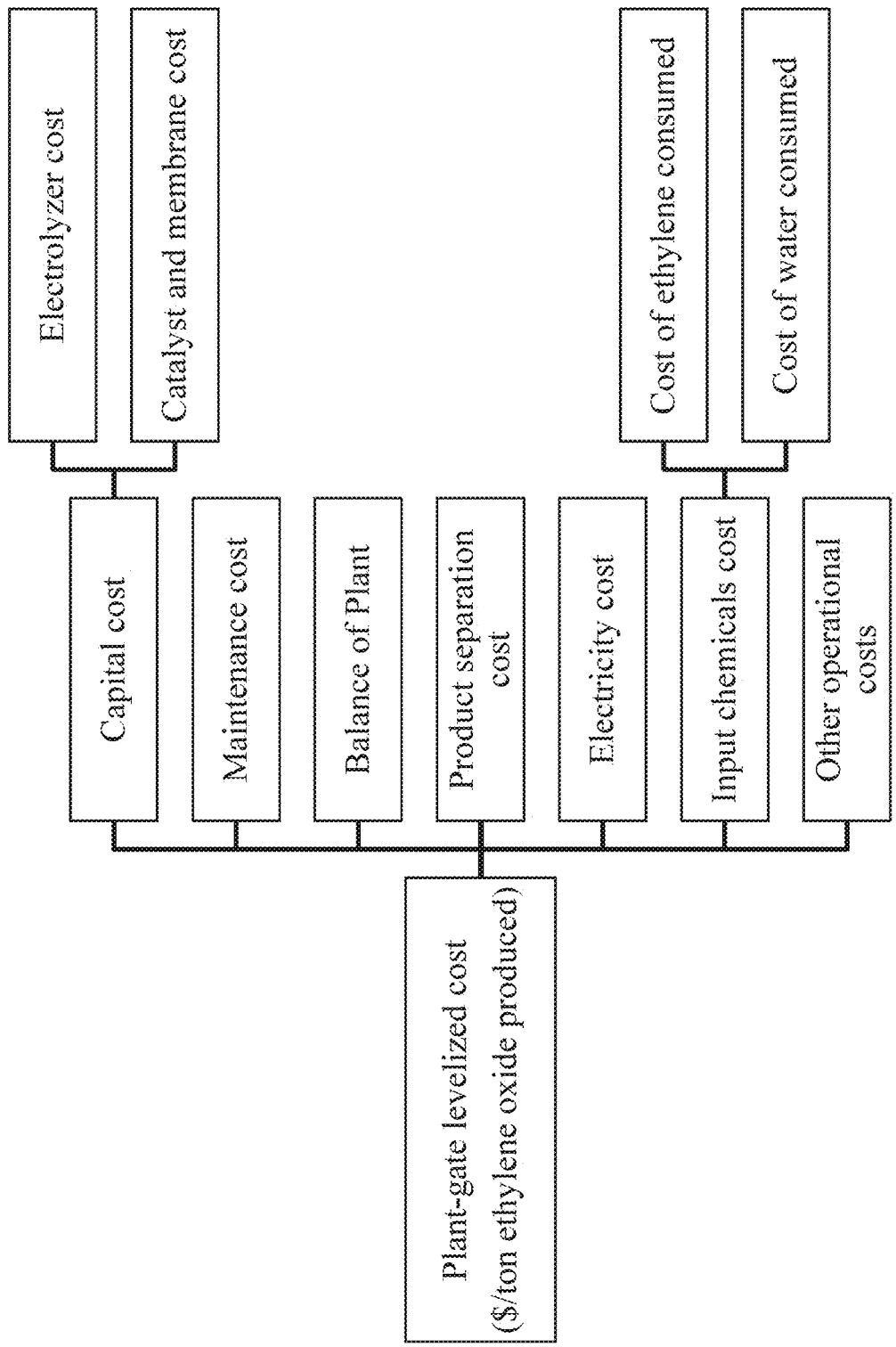
FIG. 5. Model used for the techno-economic analysis of ethylene oxide production from ethylene using electricity. Units are US$ per ton of ethylene oxide.

Techno-economic analysis (TEA) indicates conditions that could enable the profitable synthesis of a renewable-energy-powered anodic partial oxidation of ethylene to ethylene oxide (see Supplementary Materials for full details of TEA, FIG. 5). For the TEA, this work set a base electricity cost of 10 ¢/kWh, which is at least twice the average present-day industrial electricity cost (6) (FIG. 1B): recent advances in renewable technology have driven prices lower in many jurisdictions (15). Sensitivity analysis reveals that the greatest dependency of the plant-gate levelized cost is on electrochemical parameters such as current density and Faradaic efficiency (FIG. 1B, see Table 1 for range of values considered for each parameter). Based on the current market price per ton of ethylene oxide and the corresponding quantity of hydrogen produced at the cathode, it was determined that for a current density of 300 $mA/cm^2$, the minimum energy efficiency required for the renewable energy-powered process to be profitable is ~30%. This work also calculated the minimum energy efficiencies required to be profitable for different electricity costs up to 20 ¢/kWh, showing profitable regions as a function of energy efficiency and electricity cost (FIG. 1C).

The electrosynthesis of ethylene oxide involves the partial oxidation of ethylene, an anodic reaction. Reactions of this nature at high current density and Faradaic efficiency are hampered by two challenges. Firstly, the large positive potentials applied mean that uncontrolled over-oxidation often occurs, generating undesired byproducts such as $CO_2$. Currently, reported anodic upgrading reactions such as the oxidation of 5-hydroxymethylfurfural (16-18), alcohol (19-21) and glycerol (22-24), are conducted at low current densities (<100 $mA/cm^2$), since at these low current densities, high Faradaic efficiencies toward the target product have been obtained (FIG. 1D). However, the production of industrially-relevant quantities of the product at such low current densities would require unreasonably high electrolyzer surface areas, leading to high capital costs per unit of productivity (FIG. 1E). Secondly, if the reactant has limited solubility in the aqueous electrolyte (in this case, ethylene), the system quickly becomes mass-transport-limited, resulting in poor Faradaic efficiency at high current density.

TABLE 1

Range of values for sensitivity analysis.

|  | Better | Base | Worse |
| --- | --- | --- | --- |
| Ethylene cost ($/ton) | 800 | 900 | 1000 |
| Renewable electricity cost (¢/kWh) | 5 | 10 | 15 |
| Faradaic efficiency (%) | 80 | 70 | 40 |
| Current density ($mA/cm^2$) | 1000 | 300 | 50 |
| Cell potential (V) | 2.5 | 3.0 | 5.0 |
| Catalyst life time (years) | 5 | 3 | 1 |
| Electrolyzer cost ($/m^2$) | 9000 | 10000 | 11000 |

Figure 2A:
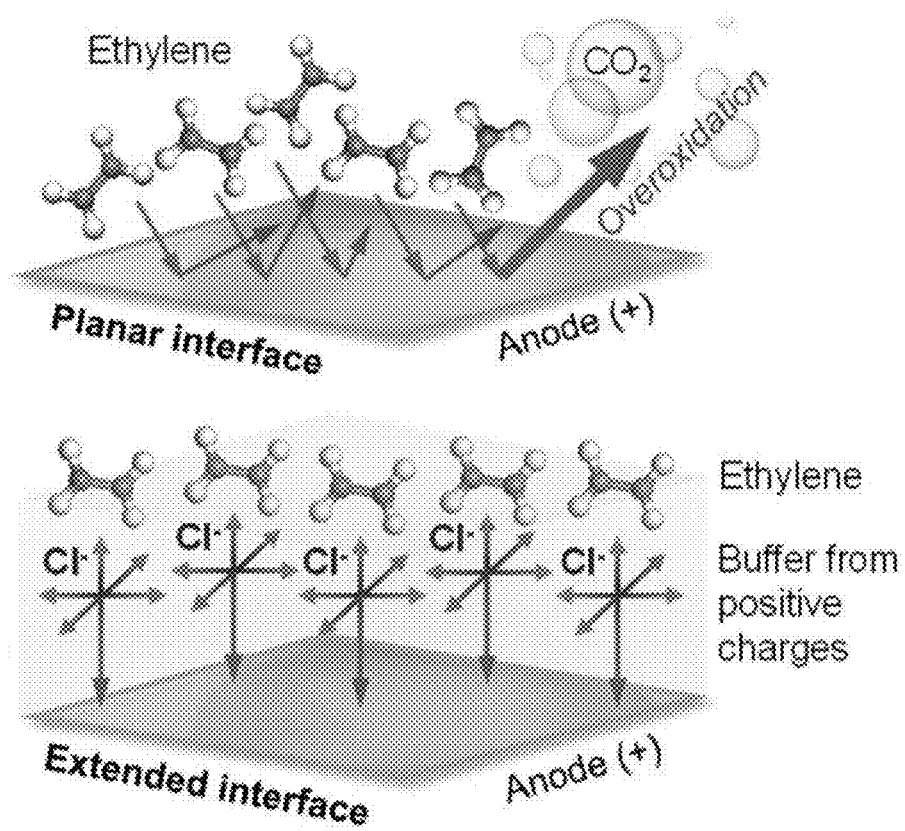
FIG. 2. Selective ethylene oxide production from ethylene enabled by an extended heterogenous:homogenous interface. (A) Schematic illustrating ethylene oxidation at planar versus extended interfaces. (B) Schematic of the ethylene-to-ethylene oxide electrochemical system. For detailed schematic see FIG. 7. (C) Faradaic efficiencies of ethylene oxide and ethylene chlorohydrin at different current densities. (D) $^{13}$C NMR spectra of ethylene oxide and ethylene chlorohydrin. (E) Faradaic efficiencies of propylene oxide and propylene chlorohydrin at different current densities.

The view was taken that, desirably, a new, selective, production strategy would avoid directly oxidizing the organic reactant molecules on the electrode surface so as to prevent over-oxidation at high current densities. This work reasoned that a positive charge reservoir that facilitates the indirect exchange of electrons between the electrode and the substrate molecules would allow this. Furthermore, in such a scheme, the space in which the reaction takes place is not limited to the planar electrode: electrolyte interface, but in fact extends into the bulk electrolyte, constituting an extended heterogeneous:homogeneous interface (FIG. 2A). This allows mass transport limitations to be overcome. Utilizing this strategy, it was demonstrated that ethylene oxide production at high current density (up to 1 A/cm$^2$) and Faradaic efficiency (~70%).

Figure 2B:
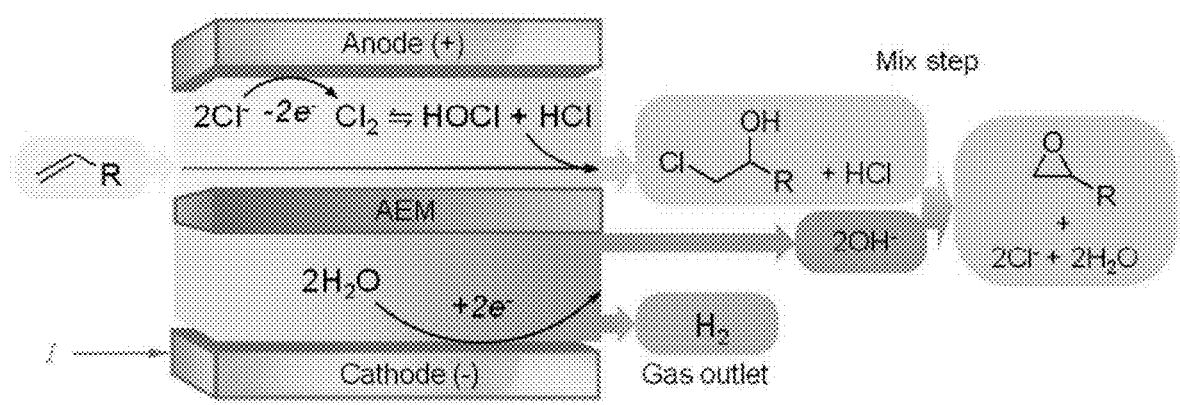
Figure 6A:
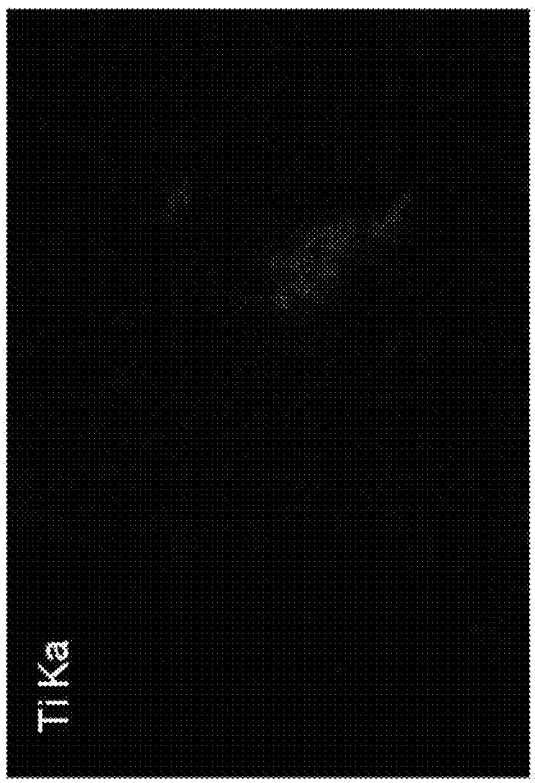
FIG. 6. (A) SEM and EDX images showing the nanostructured surface and distribution of Pd and Ti on the Pd/Ti mesh. (B) Faradaic efficiencies obtained with various strategies at 300 mA/cm$^2$. (C) Increasing half-cell potential due to Pd dissolution.
Figure 6A:
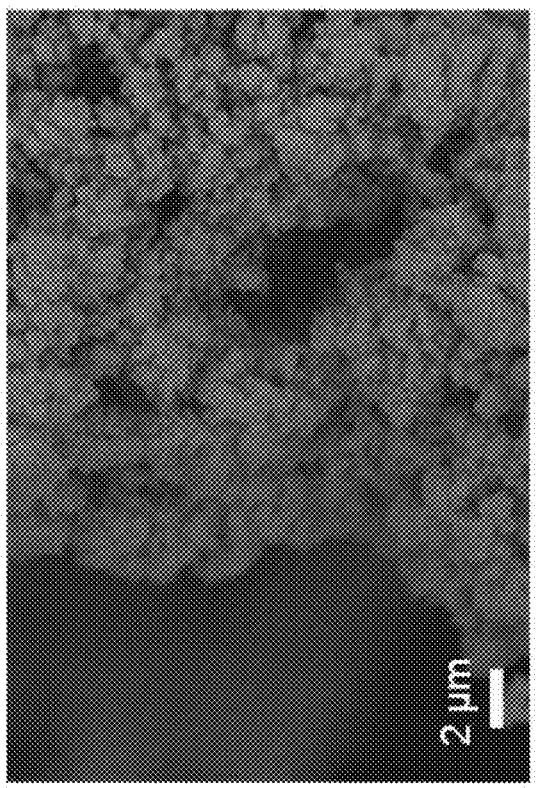
Figure 6A:
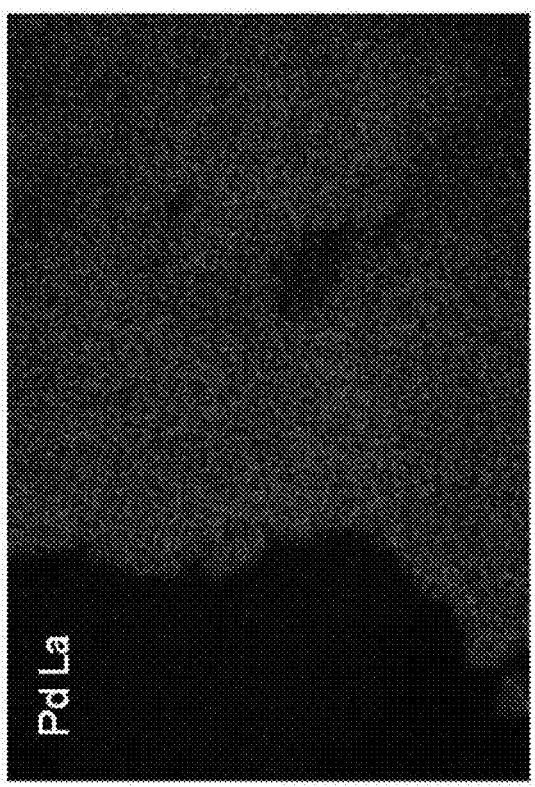
Figure 6B:
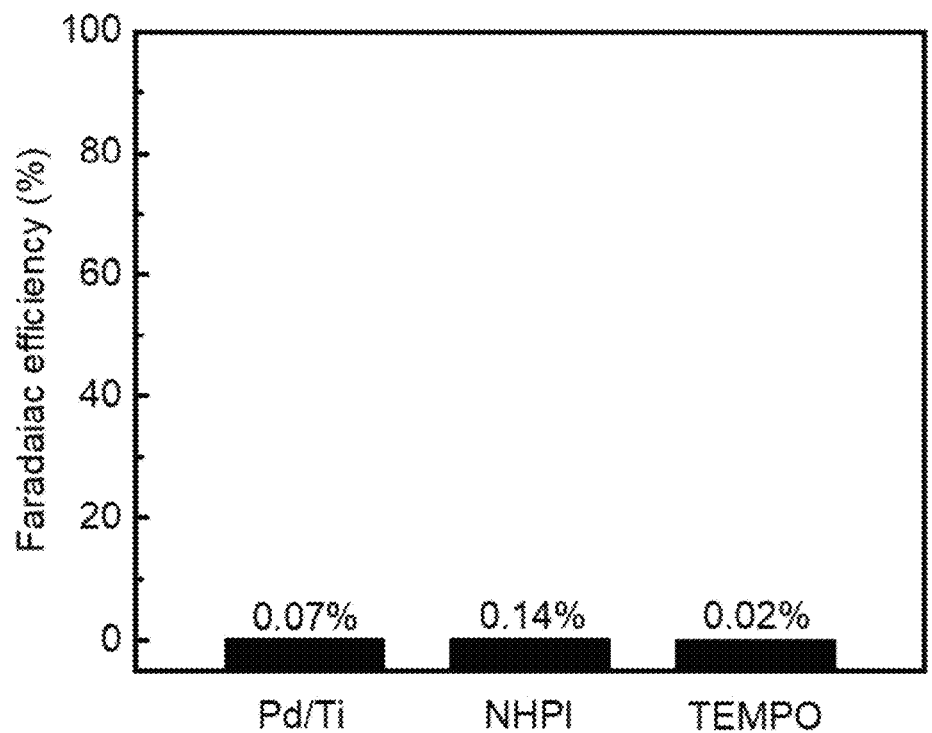
Figure 6C:
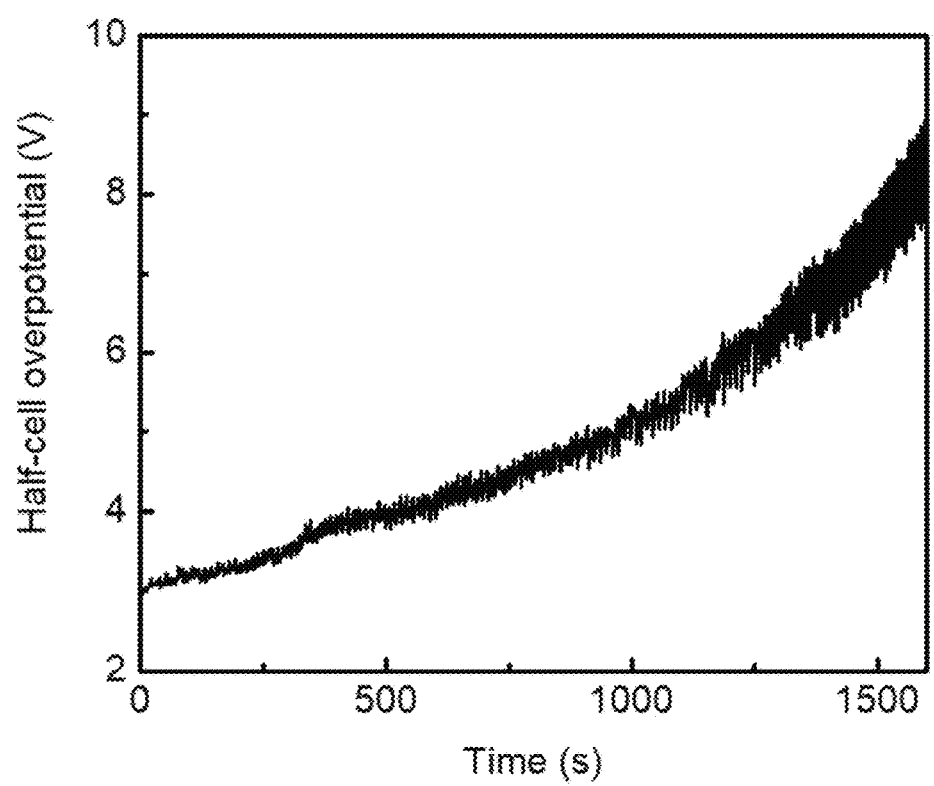

Initially it was attempted to oxidize ethylene directly to ethylene oxide using a nanostructured palladium anode (FIG. 6A). This was based on a recent study in which olefins such as propylene were oxidized at low current densities. This method did not translate to the high current densities: at 300 mA/cm$^2$, a negligible Faradaic efficiency was obtained toward ethylene oxide (FIG. 6B). Operating at this high current density resulted in dissolution of the Pd anode, as can be observed from the rapidly increasing potential with time (FIG. 6C). Additionally, the use of organic mediators such as TEMPO and NHP—a method to obtain high selectivities for partial oxidation products at the anode—failed in the generation of ethylene oxide and yielded instead only small amounts of acetate (FIG. 2B).

Figure 7:
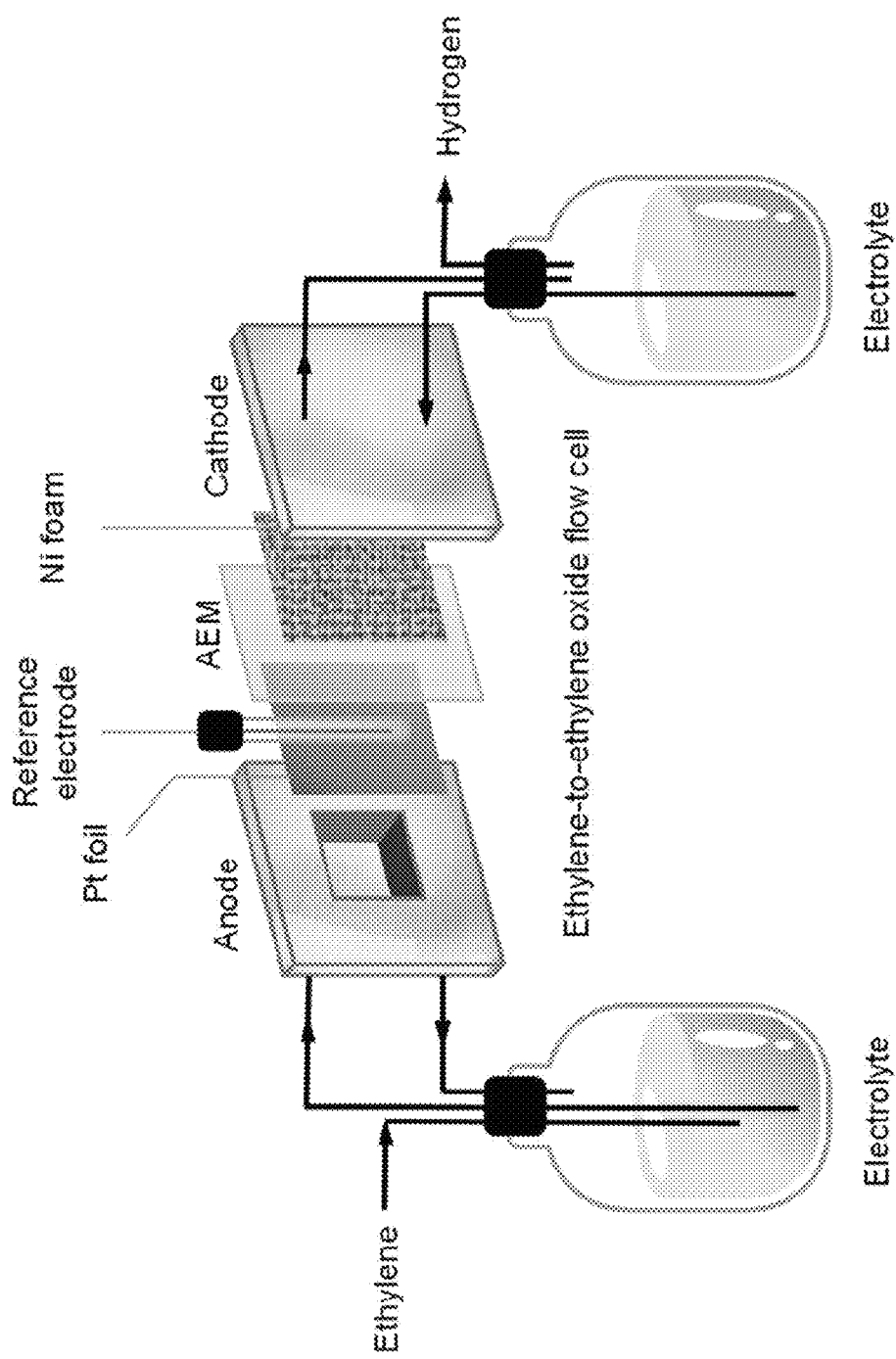
FIG. 7. Detailed schematic of the ethylene-to-ethylene oxide electrochemical flow cell system employed in this work.

It was postulated that Cl$^-$ can be a reservoir for positive charges from the anode and create an extended heterogeneous:homogeneous interface. Cl-stores and redistributes positive charges to ethylene, thereby buffering it from uncontrolled oxidation and facilitating ethylene oxide production. This idea was tested in a flow-cell setup with 1.0 M KCl electrolyte, in which ethylene was continuously sparged into the anolyte, with Pt foil as the working electrode (anode), Ni foam as the counter electrode (cathode), Ag/AgCl (3.0 M KCl) as the reference electrode (FIG. 7). An anion exchange membrane (AEM) separates the anolyte and catholyte chambers. Unless otherwise stated, all electrolysis experiments were run for a duration of 1 h.

In this case, Cl$^-$ is oxidized to Cl$_2$ at the Pt anode (Equation 1), which disproportionates in the aqueous environment to form HOCl and HCl (Equation 2) (32). HOCl then reacts with ethylene dissolved in the electrolyte to form ethylene chlorohydrin (Equation 3) (33). Since HCl is not consumed, the pH of the anolyte becomes acidic at the end of electrolysis (pH 1.1).

$$2Cl^- \rightarrow Cl_2 + 2e^- \quad (1)$$

$$Cl_2 + H_2O \leftrightarrows HOCl + HCl \quad (2)$$

$$C_2H_4 + HOCl \rightarrow HOCH_2CH_2Cl \quad (3)$$

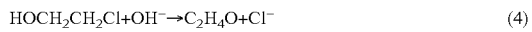

$$HOCH_2CH_2Cl + OH^- \rightarrow C_2H_4O + Cl^- \quad (4)$$

Figure 2C:
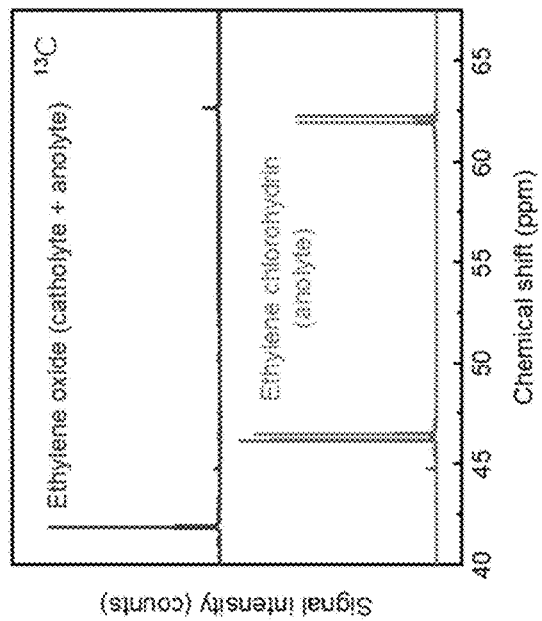
Figure 8A:
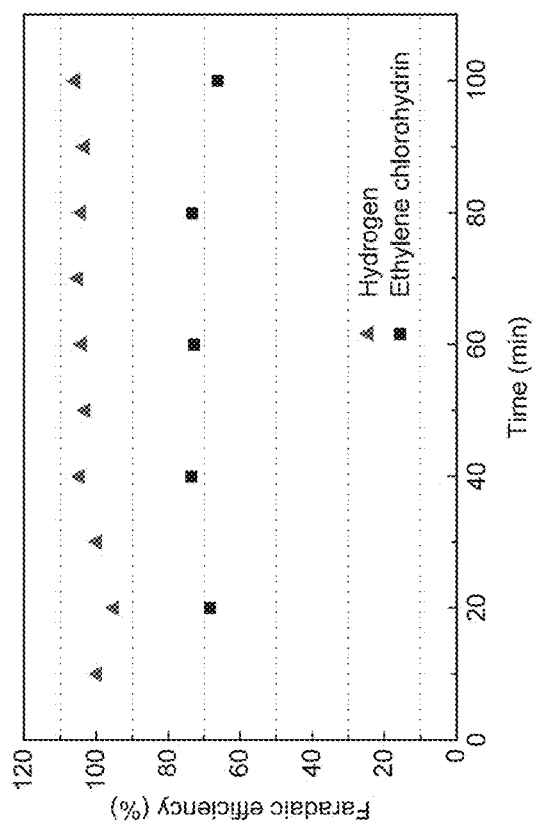
FIG. 8. (A) Faradaic efficiencies of H$_2$ and ethylene chlorohydrin as a function of time. (B) Faradaic efficiencies of ethylene oxide and ethylene chlorohydrin with different membrane types. The bipolar membrane (BPM) introduces OH-into the anolyte, which reacts with dissolved Cl$_2$ to form hypochlorite ClO$^-$, thus inhibiting the formation of ethylene chlorohydrin. The cation exchange membrane (CEM), Nafion, inhibits OH-crossover and therefore has a higher faradaic efficiency than that of the anion exchange membrane (AEM) by ~8%, indicating a small amount OH-crossover with the latter. (C) Increasing half-cell potential when the Nafion membrane is used. This is due to decreasing electrolyte conductivity from depletion of Cl$^-$ and K$^+$ (transported across membrane) in the anolyte. Hence the use of AEM is still favored for preventing conductivity loss and maintaining a steady supply of Cl$^-$.
Figure 8C:
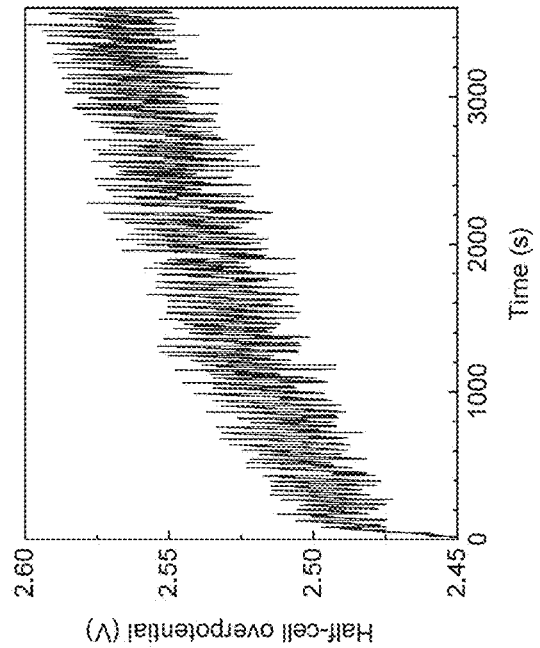
Figure 8B:
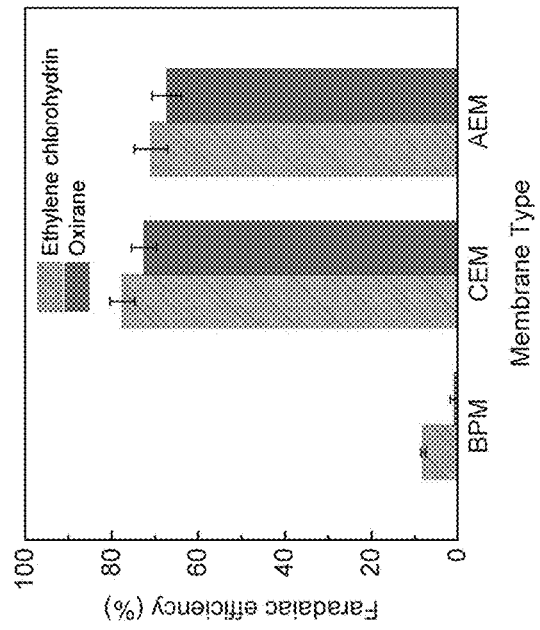

The final step (Equation 4) involves addition of alkali (OH$^-$), which then reacts with ethylene chlorohydrin to yield the desired ethylene oxide and regenerate Cl$^-$ (33): the hydrogen evolution reaction (FIG. 8A) at the cathode during electrolysis generates the OH$^-$ needed to do this. In this electrochemical system, an AEM is used, which prevents complete mixing of the catholyte and the anolyte. Consequently, at the end of electrolysis, the pH of the catholyte becomes alkaline with a pH value of 13.8. This means that by merging the catholyte and anolyte output streams (performed post electrolysis), ethylene oxide can be generated from the reaction between ethylene chlorohydrin and OH$^-$ (FIG. 2C). It can be noted that in principle, a cation exchange membrane would be better in preventing crossover of OH$^-$ (FIG. 8B). However, this leads to a continuous decrease in electrolyte (anolyte) conductivity during operation, resulting in lowered performance (see FIG. 8C).

Figure 2D:
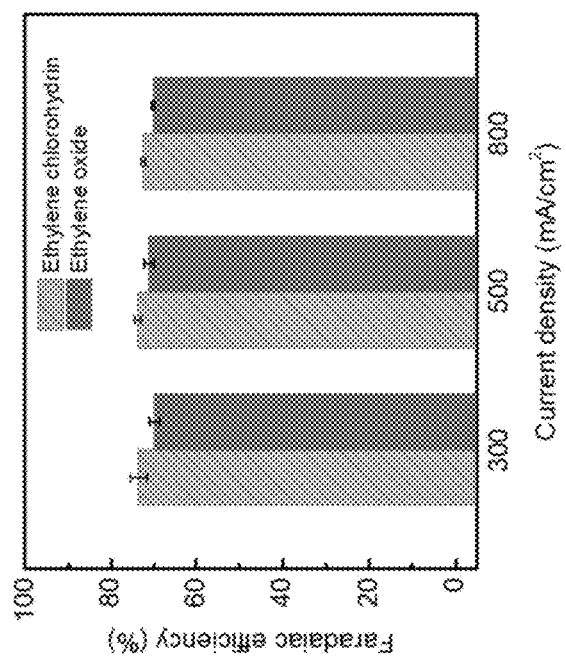
Figure 9C:
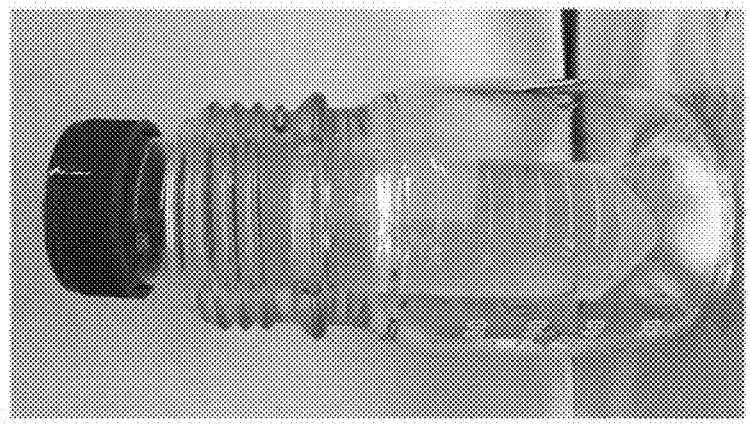
FIG. 9. (A) Digital photograph of the anolyte after addition of excess 10% KI solution. A brown coloration is observed due to oxidation of I$_-$ to form I$_2$. (B) Digital photograph of the same anolyte after starch solution was added, forming a dark blue starch-iodine complex. (C) Digital photograph of the anolyte after titration with Na$_2$S$_2$O$_3$, yielding a clear colorless solution.
Figure 9B:
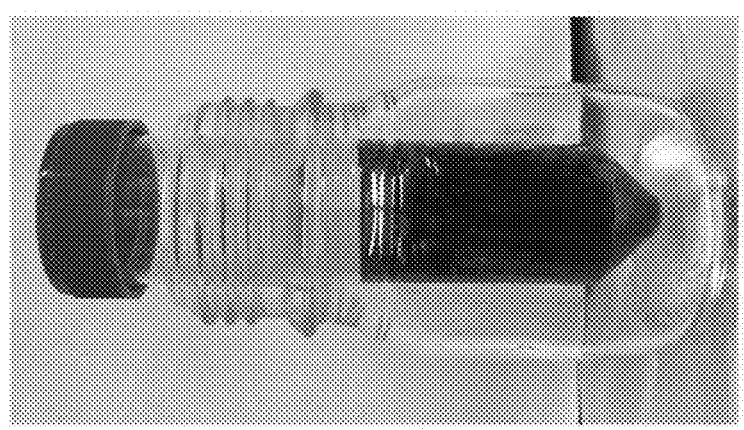
Figure 9A:
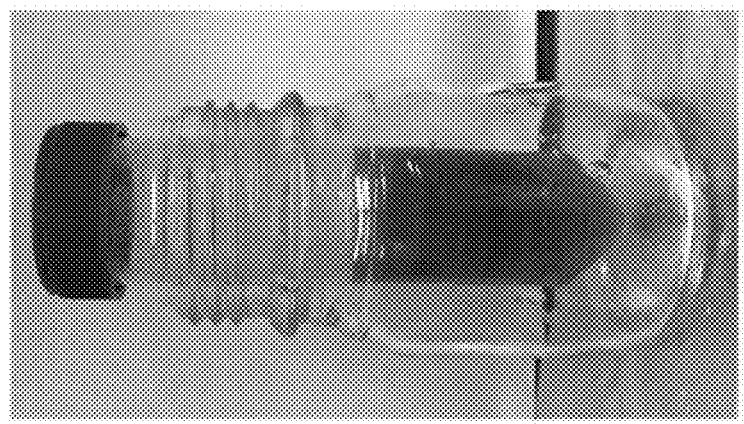

In sum, this system enables the generation of ethylene oxide in a single electrolyzer under ambient temperatures and pressures: ethylene, water and electricity are the consumables. Using this method, this work achieved a Faradaic efficiency of 70 (±1) % toward ethylene oxide (FIG. 2D) with 1.0 M KCl at 300 mA/cm$^2$. Similar Faradaic efficiencies of 71 (±1) % and 70 (±1) % are maintained even at current densities of 500 and 800 mA/cm$^2$, respectively (FIG. 2D). A possible explanation for the missing charge could be $O_2$ evolution or complete oxidation of ethylene to form $CO_2$; however, when this work performed gas chromatography on the output gas stream, one did not detect $O_2$ nor $CO_2$. This work hypothesized that the missing charge could be due to unreacted chlorine/hypochlorite species in the electrolyte: this was confirmed using iodometric titration (see FIG. 9 and Table 2).

Figure 2E:
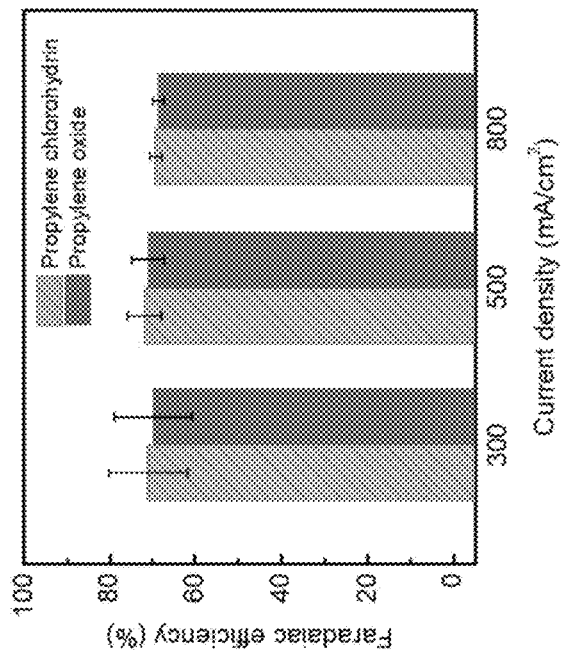
Figure 10A:
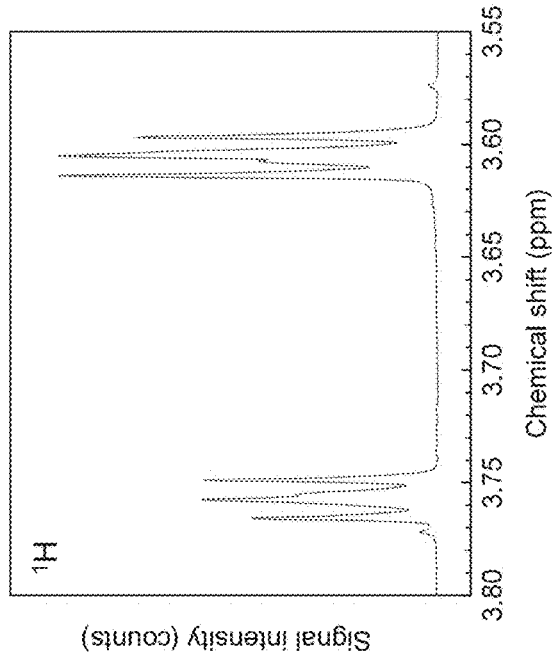
FIG. 10. (A) 1H NMR spectra of ethylene oxide and ethylene chlorohydrin. (B) Close-up of the characteristic features of ethylene chlorohydrin in the $^1$H NMR spectra. (C) $^1$H NMR spectra of $^{13}$C$_2$H$_4$O (ethylene oxide) and $^{13}$C$_2$H$_5$ClO (ethylene chlorohydrin) generated from electrolysis experiments using $^{13}$C$_2$H$_4$.
Figure 10B:
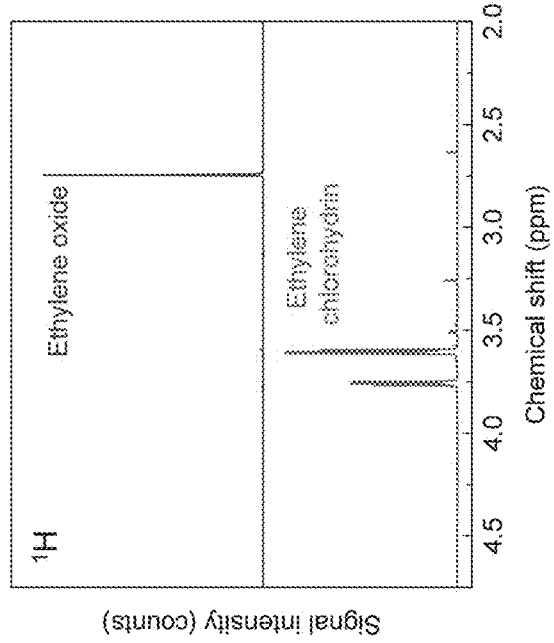
Figure 10C:
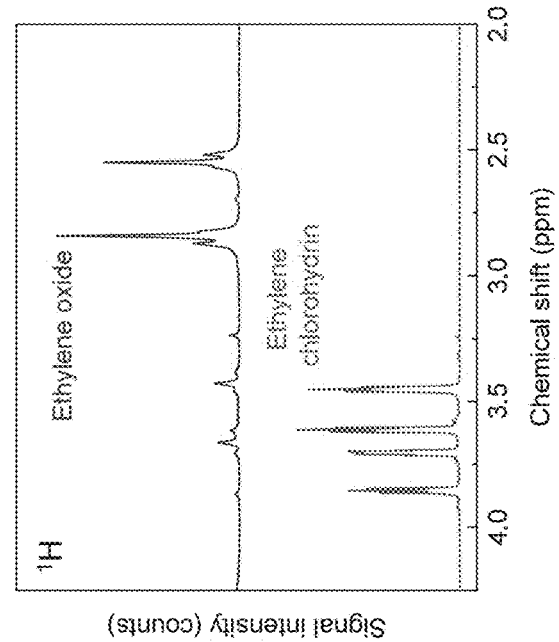
Figure 11A:
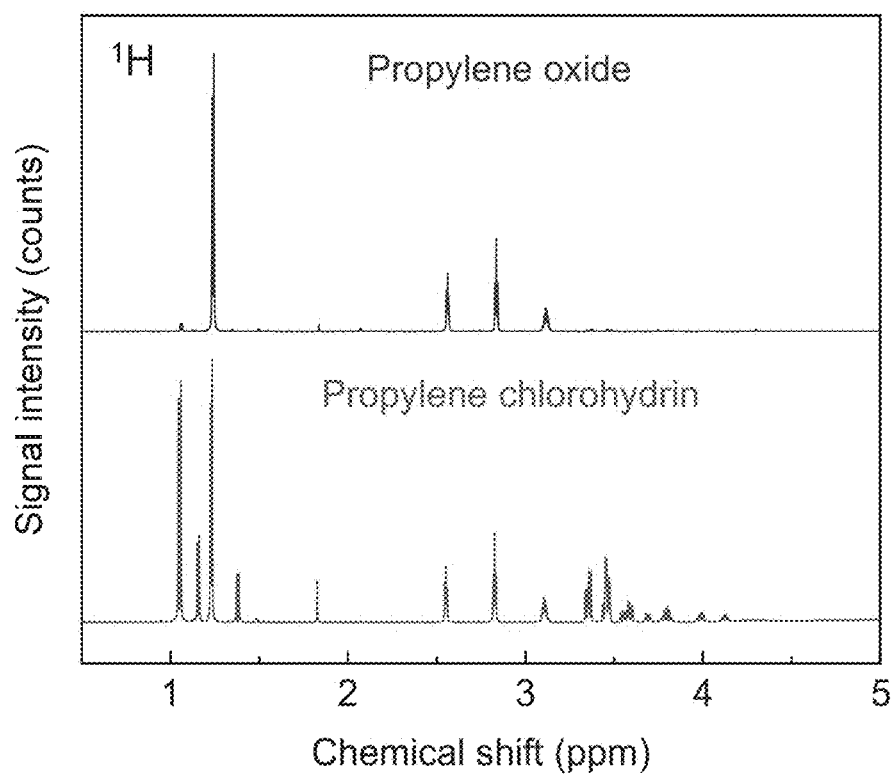
FIG. 11. (A) 1H NMR spectra of propylene oxide and propylene chlorohydrin. (B) Techno-economic analysis (TEA) of propylene oxide production showing plant-gate levelized cost as a function of energy efficiency and renewable energy cost.
Figure 11B:
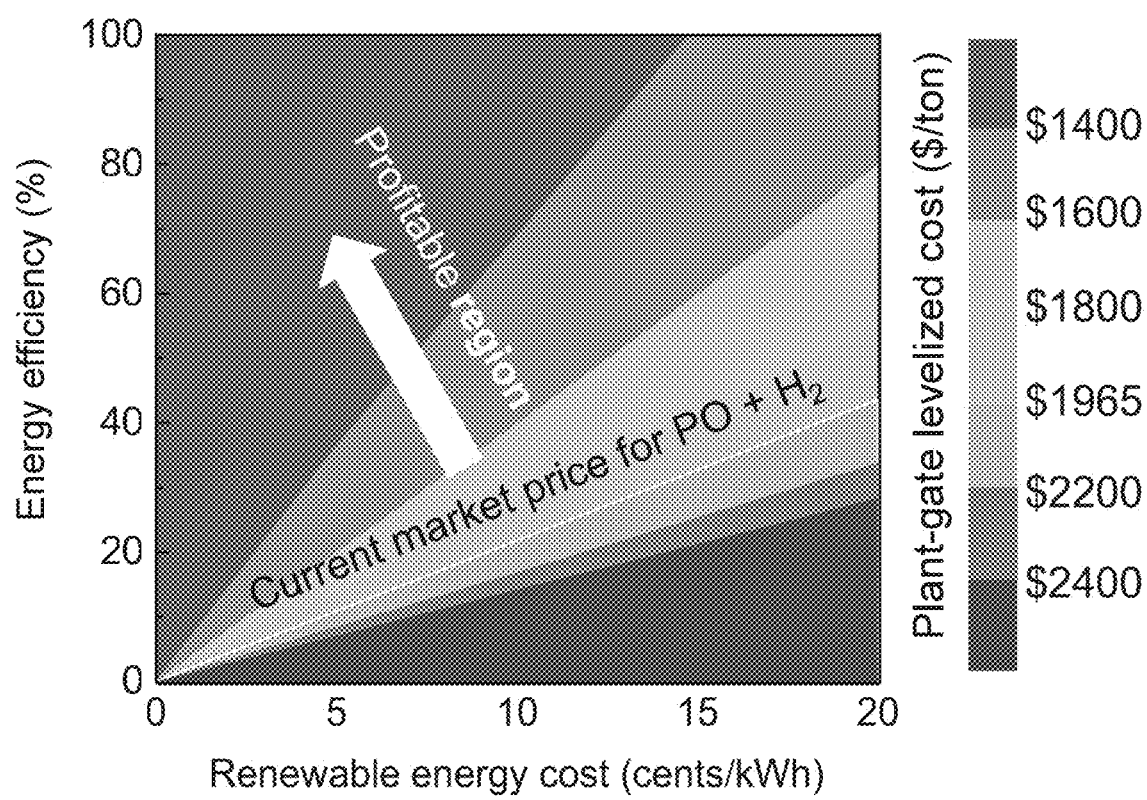

This work performed the same experiments but using carbon-13 labelled ethylene ($^{13}C_2H_4$): $^{13}C$ NMR and $^1H$ NMR results confirm that the products observed are indeed due to the partial oxidation of ethylene (FIG. 2E and FIG. 10). The method could also be used for the epoxidations of other olefins; for instance, when one replaces ethylene with propylene, Faradaic efficiencies are 69-71% toward propylene oxide—a commodity chemical with a 10 million ton per annum market in the plastics industry (34)—at current densities of 300-800 mA/cm$^2$ (FIG. 2F and FIG. 11).

Figure 1B:
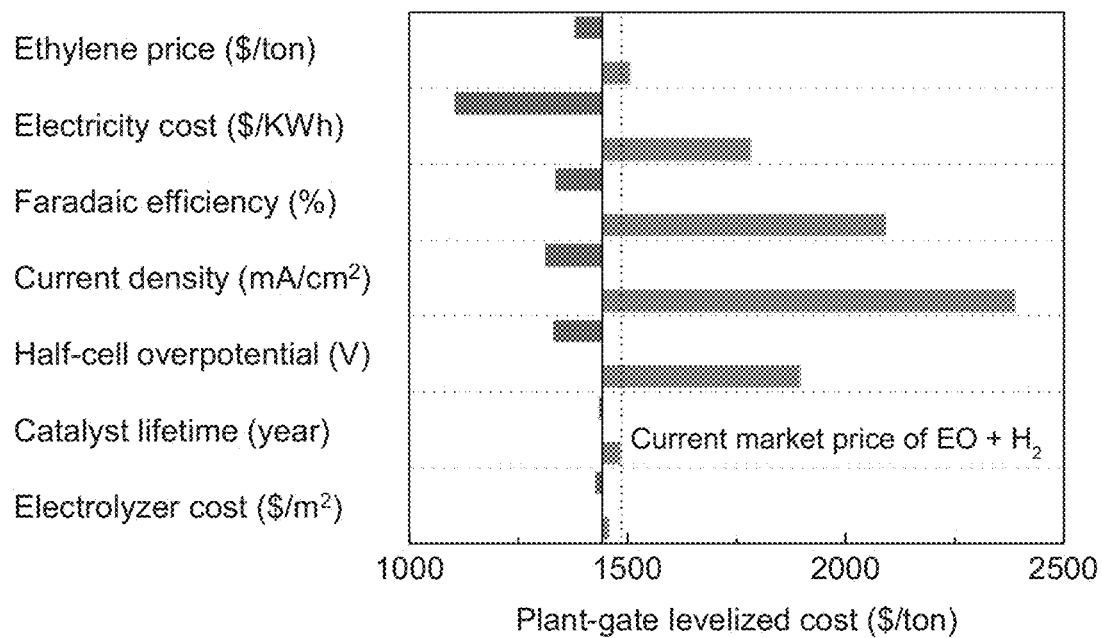
Figure 1C:
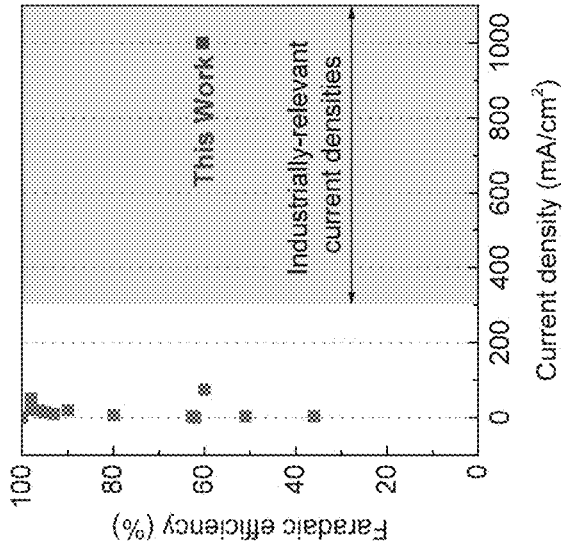
Figure 1D:
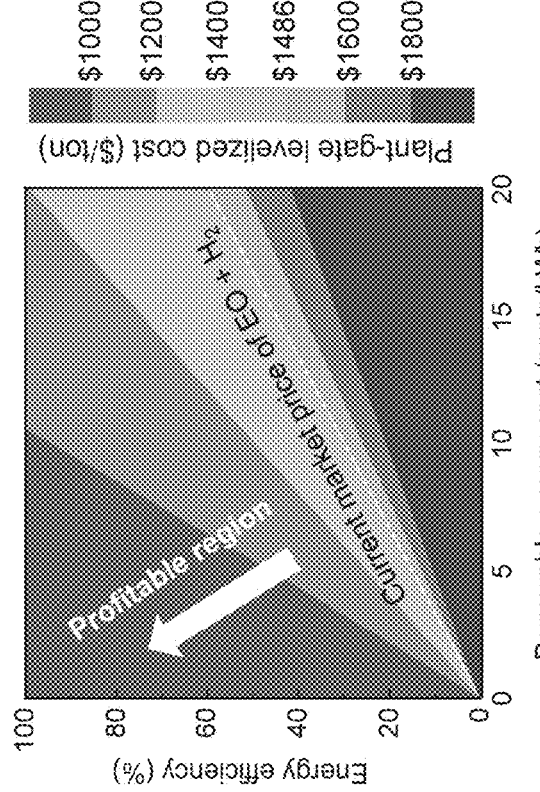
Figure 1E:
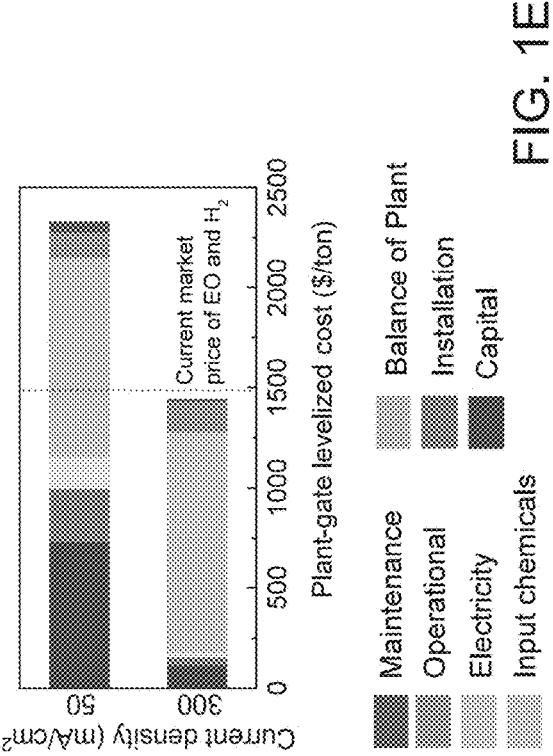
Figure 3A:
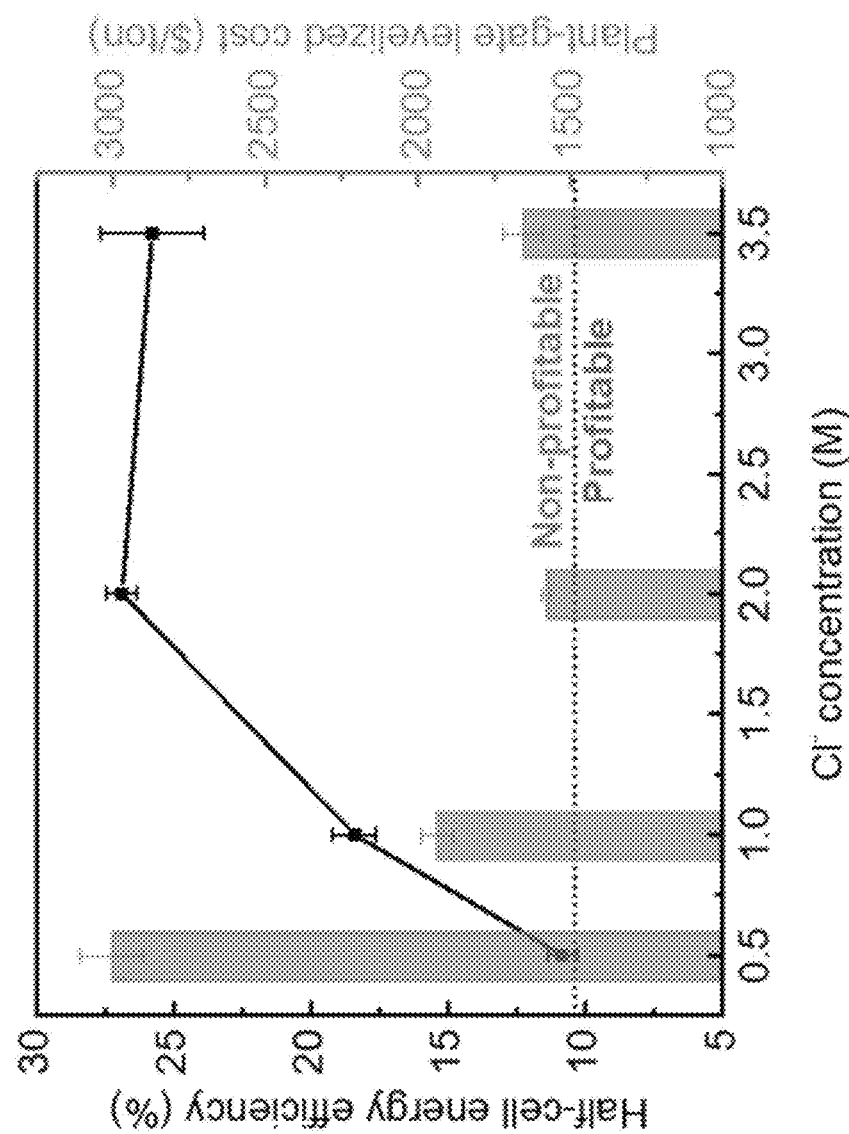
FIG. 3. Optimization of energy efficiency to reduce energy cost and maximize technoeconomic benefit. (A) Half-cell energy efficiency and the corresponding plant-gate levelized cost as a function of Cl$^-$ concentration. XPS spectra of (B) Ir 4f, (C) Ti 4f and (D) O 1s. (E) SEM image of the IrO$_2$/Ti mesh. (F) EDX images showing the distribution of Ir, Ti and O on the IrO$_2$/Ti mesh. (G) Half-cell energy efficiency and the corresponding plant-gate levelized cost as a function of current density. Note: our half-cell energy efficiencies are based on our reported potentials vs. Ag/AgCl, which are not IR-corrected. Additionally, it was assumed that no losses occurred at the cathode side, where hydrogen evolution occurs.

The sensitivity analysis of FIG. 1B revealed that the plant-gate levelized cost is sensitive to electrochemical parameters such as Faradaic efficiency and cell potential (FIGS. 1B and 1C). To reduce energy cost, it was sought to increase the energy efficiency of the reaction by varying the electrolyte concentration while operating at 300 mA/cm$^2$. This work began at lower Cl$^-$ concentration (0.5 M); however, oxygen evolution from water dominates the anodic reaction, resulting in a low Faradaic efficiency of 30 (±1) % and energy efficiency of 11 (±1) % (FIG. 3A). As the Cl$^-$ concentration increases (1.0 M and 2.0 M), the overpotential decreases (5.8 (±0.2) V and 4.0 (±0.1) V) due to improved Cl-oxidation kinetics and increased electrolyte conductivity, leading to increased Faradaic efficiencies (70 (±1) % and 67 (±1) %) and half-cell energy efficiencies (18 (±1) % and 27 (±1) %. At 3.5 M, however, the energy efficiency was unimproved at 26 (±1.9) % as the reduced potential (3.6 (±0.2) V) is negated by a slight decrease in Faradaic efficiency to 55 (±1) %, likely because the increased Cl$^-$ concentration is unfavorable for the disproportionation of Cl$_2$ into HOCl and HCl (equation 2). Thus, based on the corresponding plant-gate levelized costs, this work determined the optimal Cl$^-$ concentration to be 2.0 M. In this work all potentials are reported vs. Ag/AgCl and are not IR-corrected.

Figure 3B:
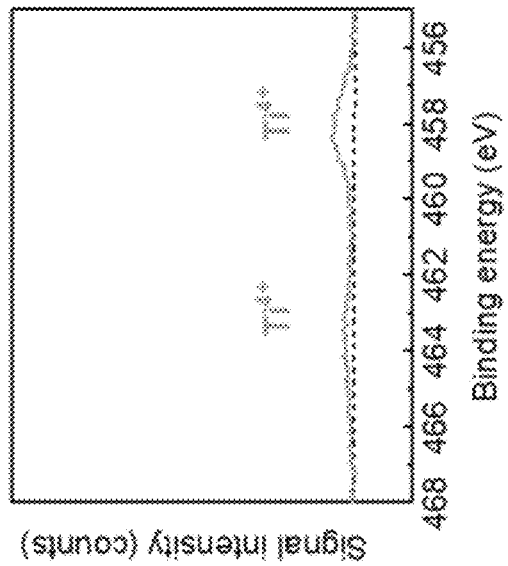
Figure 3D:
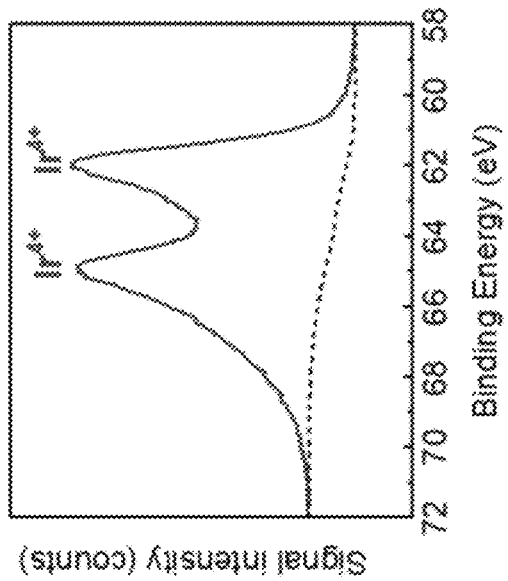
Figure 3C:
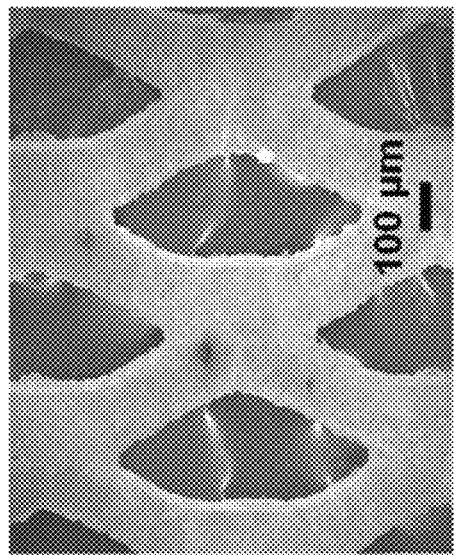
Figure 3E:
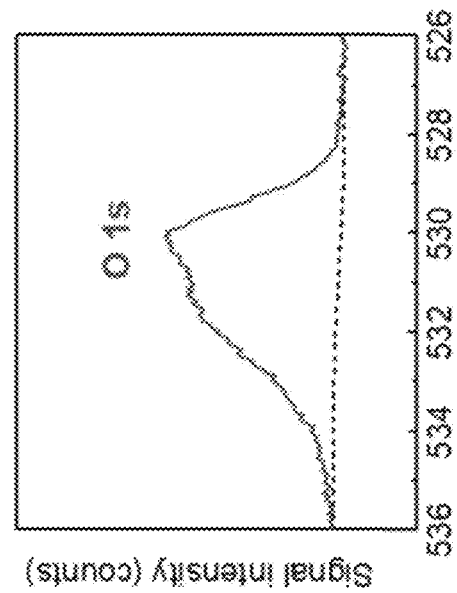
Figure 3F:
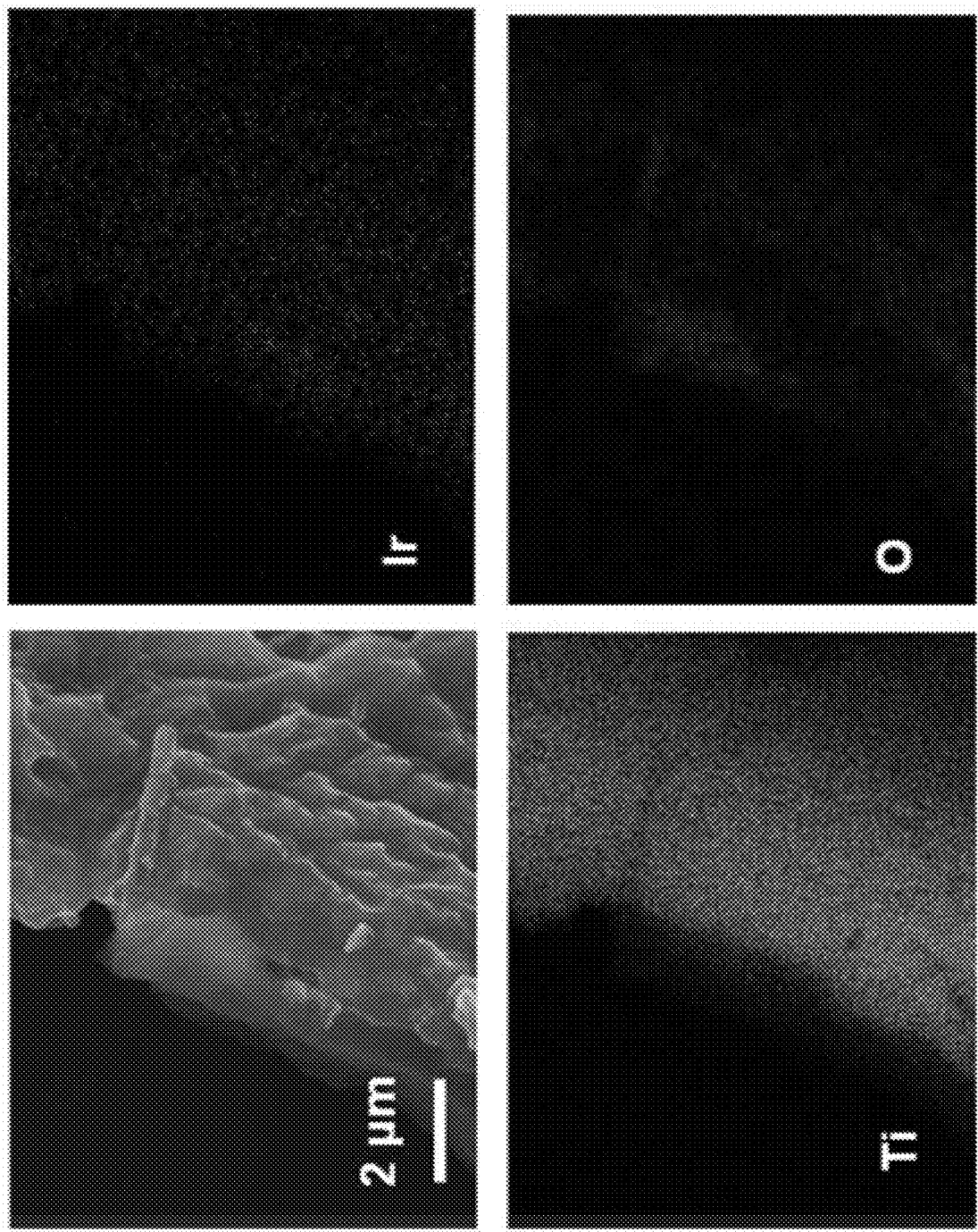
Figure 12A:
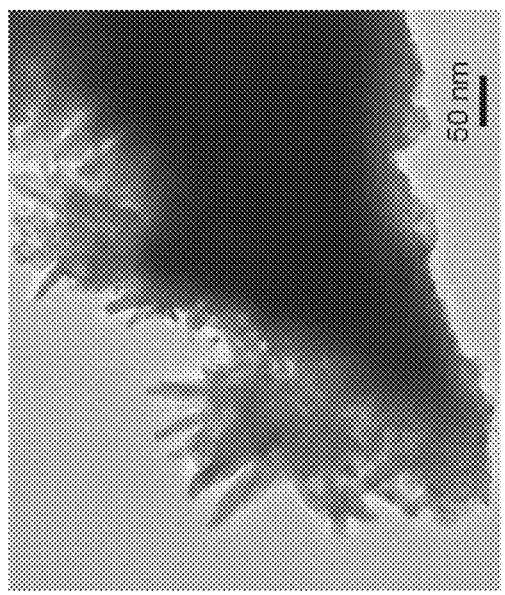
FIG. 12. (A) XRD spectra of the IrO$_2$/Ti mesh and IrO$_2$ particles. (B) and (C): TEM images of the IrO$_2$ particles at different degrees of magnification.
Figure 12B:
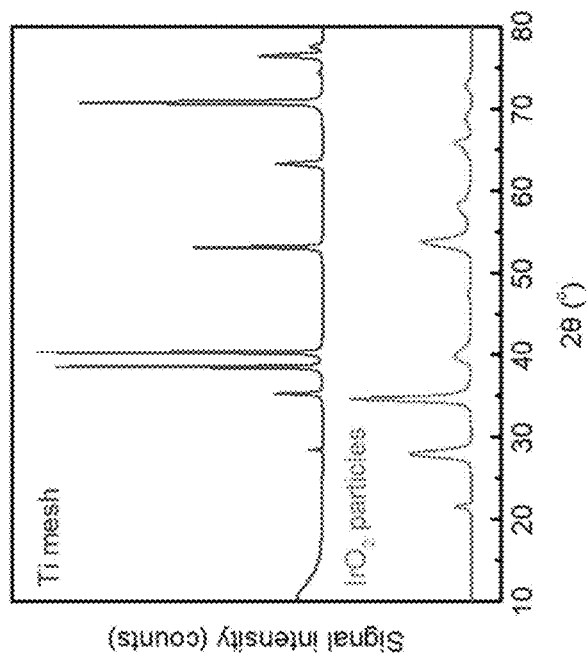
Figure 12C:
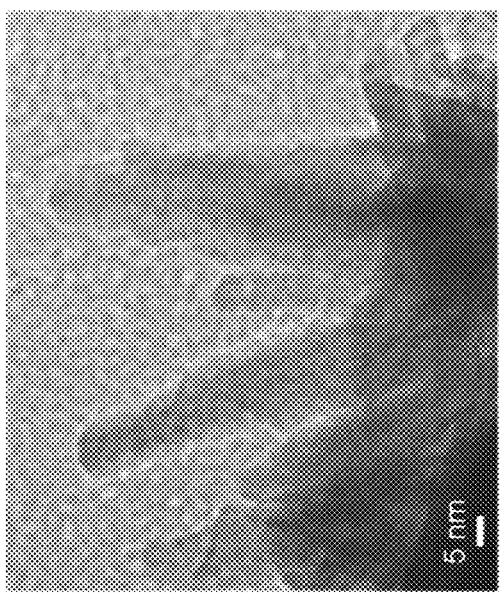

Even at the optimal Cl$^-$ concentration, the renewable electricity-based plant-gate levelized cost remains higher than the current market price per ton of ethylene oxide and the corresponding quantity of hydrogen (FIG. 3A). This work turned to the working electrode (catalyst) as another degree of freedom to decrease the overpotential. This work prepared IrO$_2$ deposited on Ti mesh (FIG. 3A) using a dip coating and thermal decomposition procedure (35). X-ray photoelectron spectroscopy (XPS) results confirm the presence of Ir in an oxidation state of 4+ (FIG. 3B-D). SEM images show the microscale mesh structure of the IrO$_2$ coated Ti mesh (FIG. 3E). Energy-dispersive X-ray spectroscopy (EDX) confirmed the presence of Ir and O on the Ti mesh, indicating the loading of IrO$_2$ on Ti (FIG. 3F). X-ray diffraction was also performed on the IrO$_2$ coating as well as the bare Ti mesh (FIG. 12A). Additionally, TEM images of the IrO$_2$ were taken as well (FIGS. 12B and 12C). Using this, this work reduced the required applied potential from 3.4 (±0.1) V to 3.0 (±0.1) V, thus further raising the half-cell energy efficiency to 30 (±1) % at 300 mA/cm$^2$.

Figure 3G:
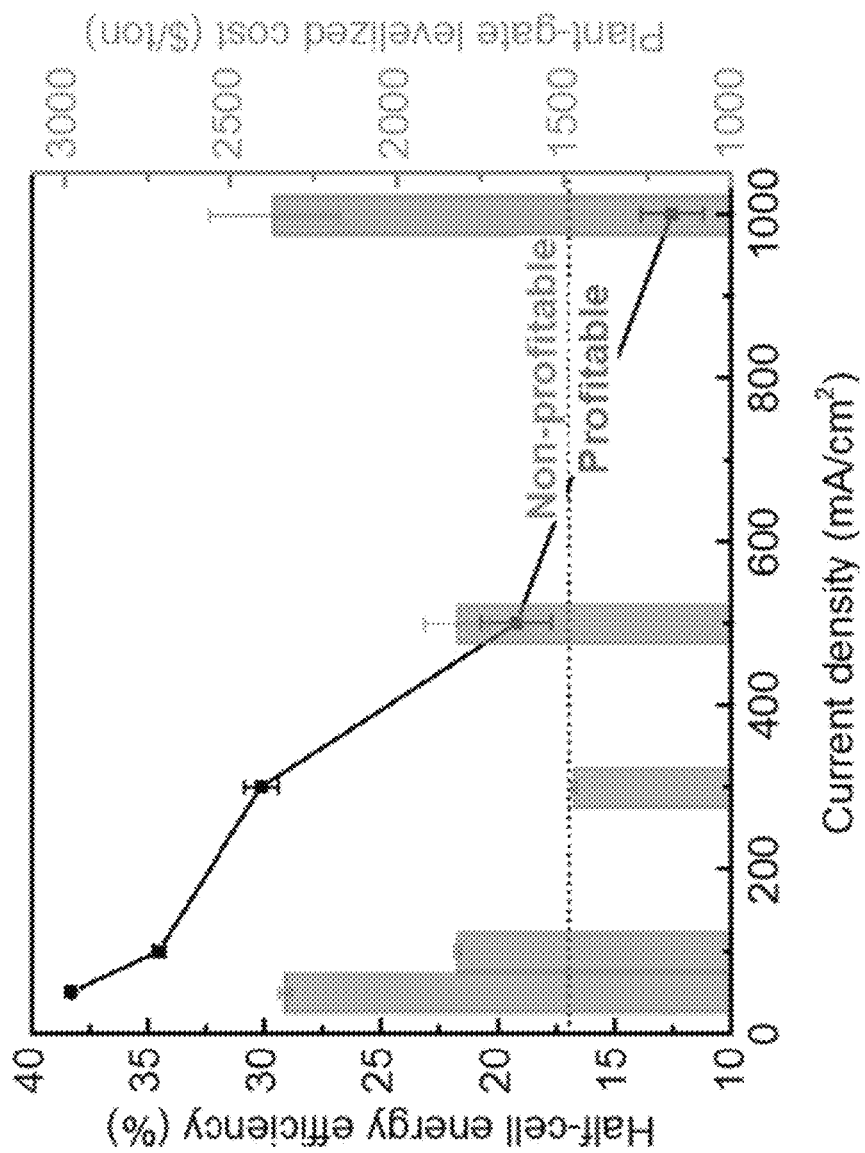

Having optimized the electrochemical system, we measured the energy efficiencies and plant-gate levelized costs under different current densities to determine the most economical conditions for industrial manufacturing (FIG. 3G). Faradaic efficiencies were maintained even at a current density of 1 A/cm$^2$ (60 (±4) %). However, a much higher potential of 6.5(±0.5) V was required to drive the larger current, leading to a low half-cell energy efficiency (12(±1) %). On the other hand, the half-cell energy efficiency is high at 38.3(±0.1) % under 50 mA/cm$^2$, thus the electricity cost per ton of ethylene oxide is at the lowest. However, the high capital cost associated with electrolyzer surface area resulted in an uneconomical plant-gate levelized cost. The plant-gate levelized cost is the lowest at 300 mA/cm$^2$; with good energy efficiency of 30 (±1) % and acceptably low capital costs.

Figure 4A:
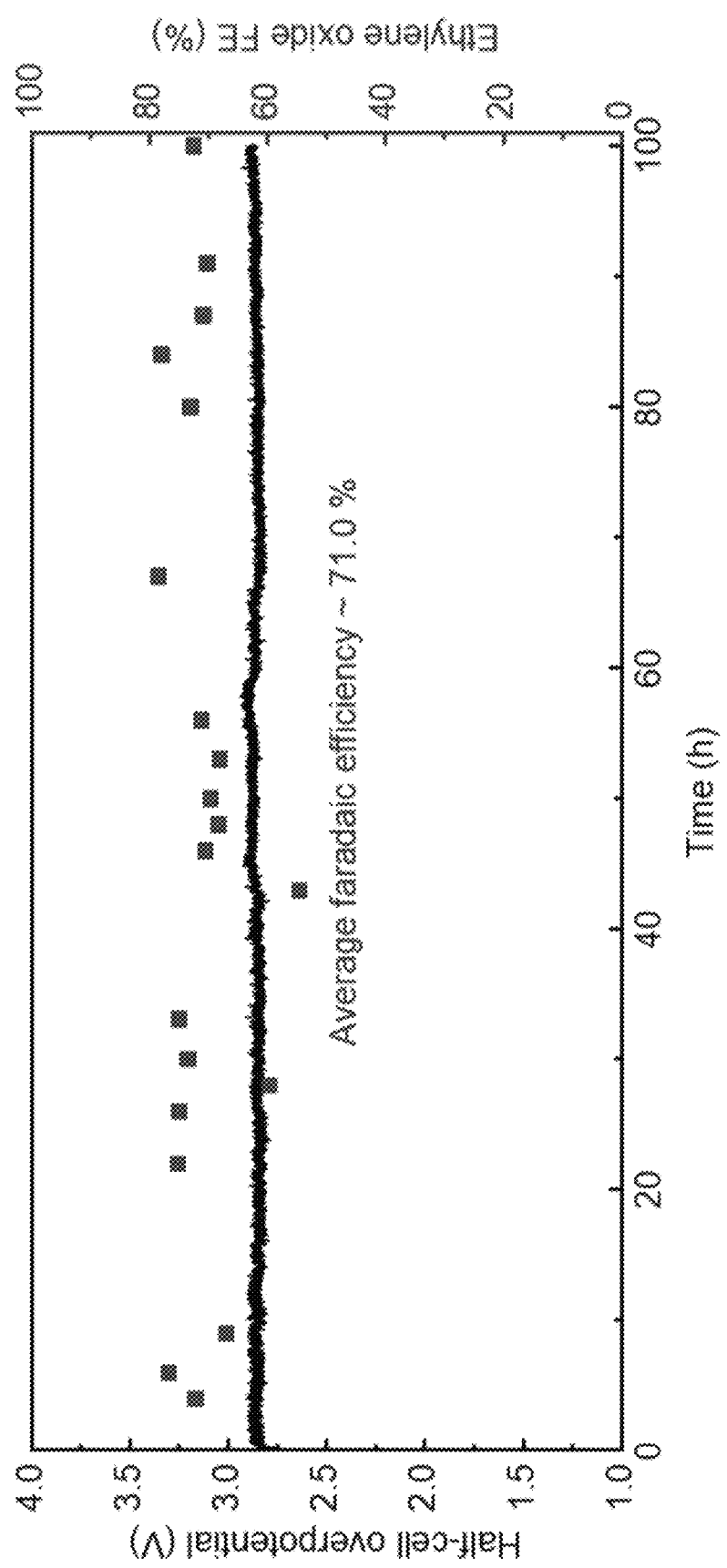
FIG. 4. Evaluation of ethylene-to-ethylene oxide performance. (A) Half-cell overpotential and Faradaic efficiency of ethylene oxide over 100 h at 300 mA/cm$^2$. (B) Comparison of current density, product generation rate, reported operation time, Faradaic efficiency and product selectivity against state-of-art anodic upgrading reactions. Specificity refers to the percentage of all reacted substrate going towards the desired product. (C) Schematic of the CO$_2$-to-ethylene oxide (EO) process in which the ethylene-to-EO cell was directly supplied with the gas output from a CO$_2$-to-ethylene MEA. (D) Faradaic efficiencies of ethylene (in MEA) and ethylene oxide (in flow cell) as a function of the gas flow rate. For all cases, the MEA was run at 240 mA/cm$^2$ and the ethylene oxidation flow cell was operated at 300 mA/cm-2 for a duration of 1 h.
Figure 4B:
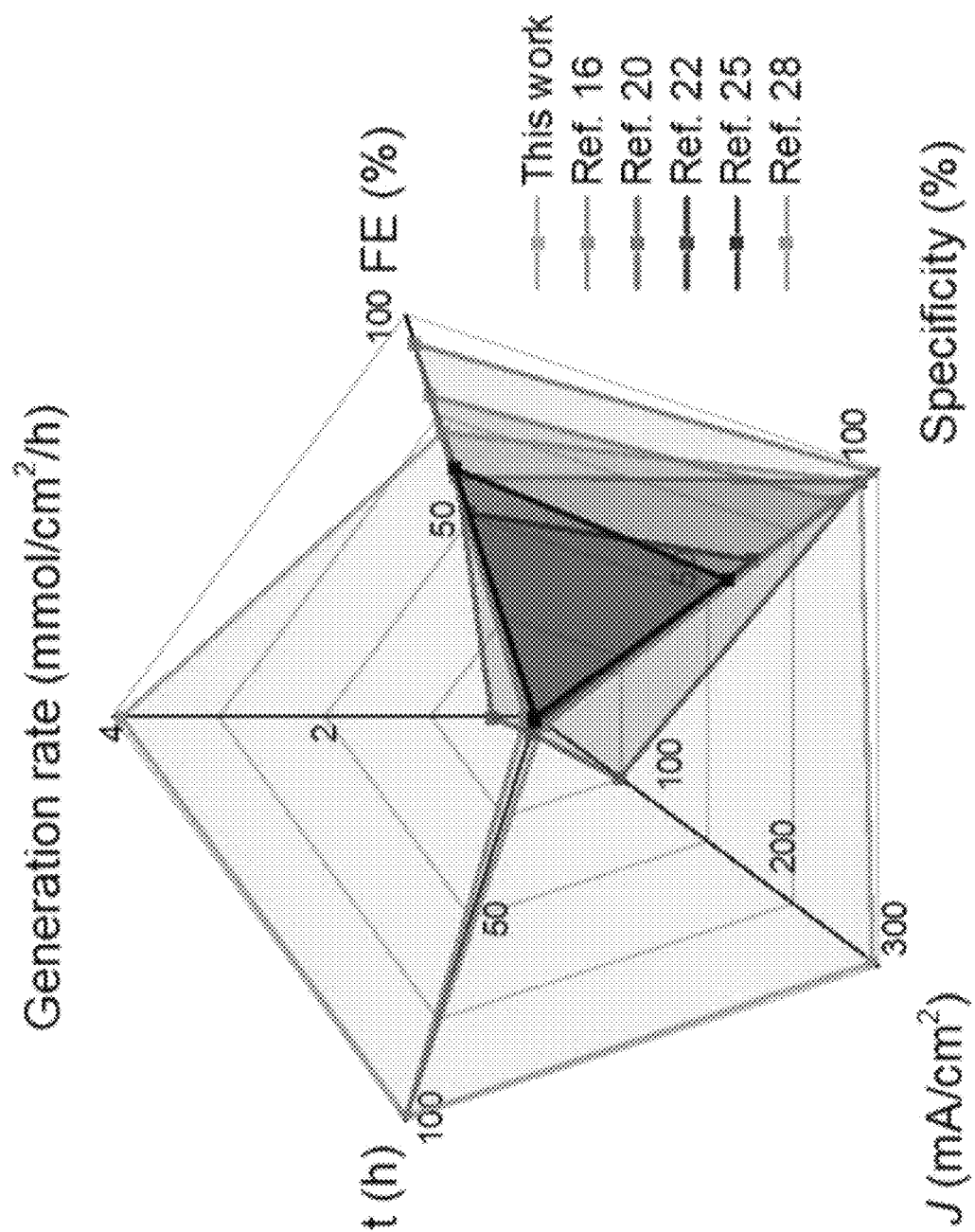
Figure 13A:
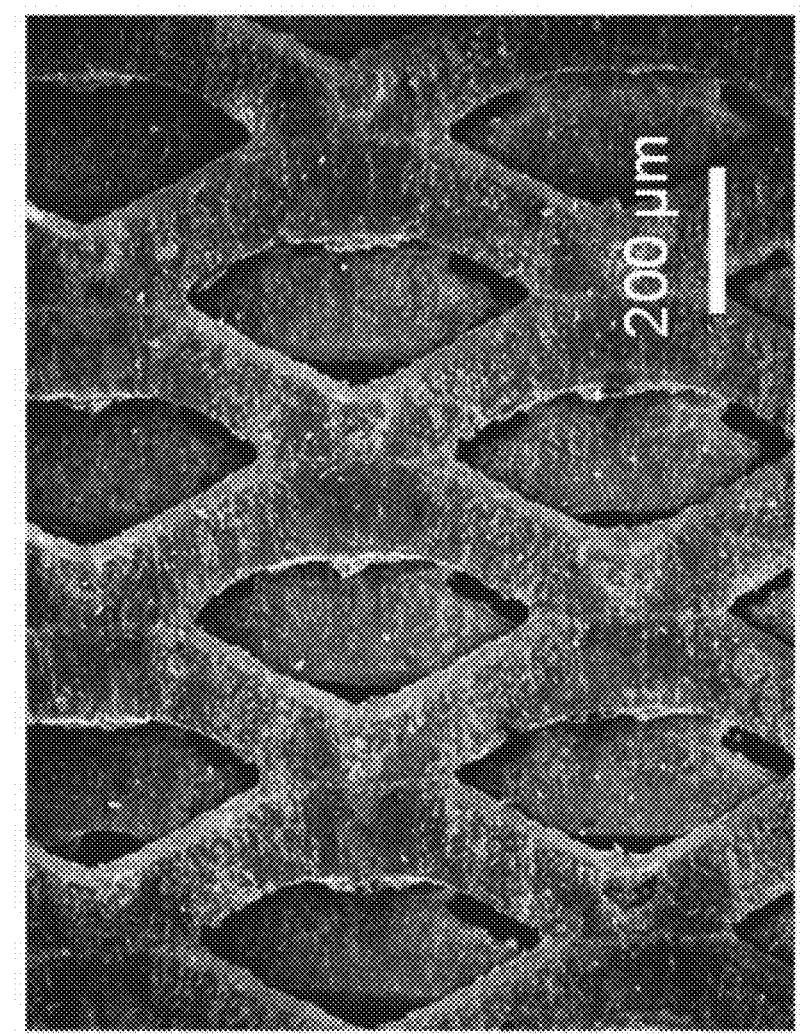
FIG. 13. (A) SEM image of the IrO$_2$/Ti mesh after electrochemical ethylene oxide production at 300 mA/cm$^2$ for 100 h. (B) EDX images showing the distribution of Ir, Ti and O on the IrO$_2$/Ti mesh after reaction.
Figure 13B:
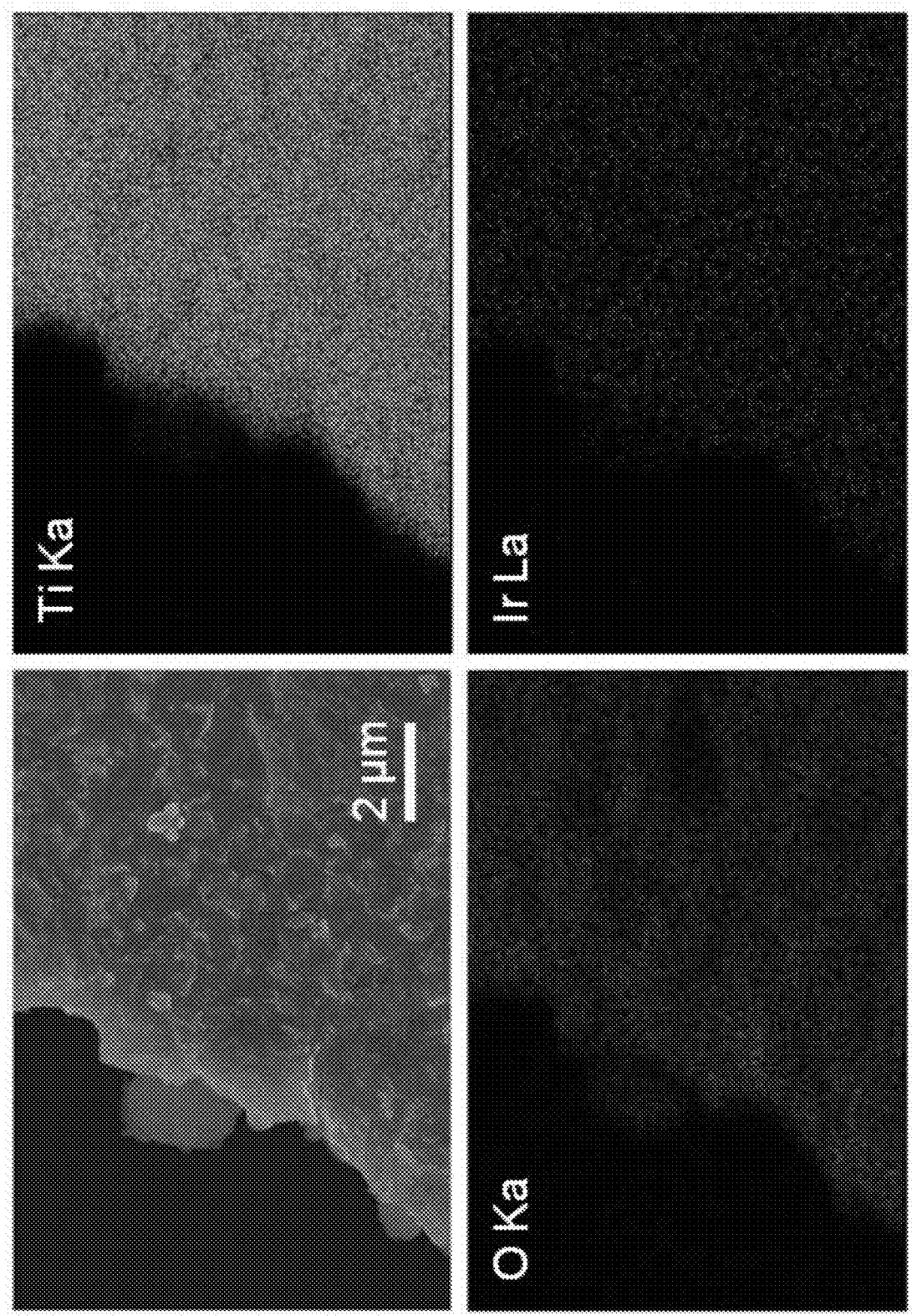

Based on this analysis, this work investigated the stability of the catalyst system at the most profitable current density of 300 mA/cm$^2$, during which portions of the electrolyte are periodically removed for analysis and replaced with fresh electrolyte. The system maintained a stable applied potential of 2.86(±0.02) V and Faradaic efficiency averaging 71(±0.6) % for 100 hours continuously. Post-reaction analysis of the anode through SEM and EDX revealed no obvious structural changes of the Ti mesh surface nor loss of $IrO_2$ (FIG. 13). The method significantly outperforms other reported anodic upgrading reactions in current density, product generation rate and reported operation time, while maintaining Faradaic efficiency and ethylene oxide specificity (FIG. 4B). In this case, specificity refers to the percentage of reacted substrate (ethylene) that goes to the desired product. The specificity in this case is 100%, since one does not observe the conversion of ethylene to other products (e.g. $CO_2$). This is important in an industrial process, since the ethylene will likely be continuously recirculated to maximize usage.

Figure 4C:
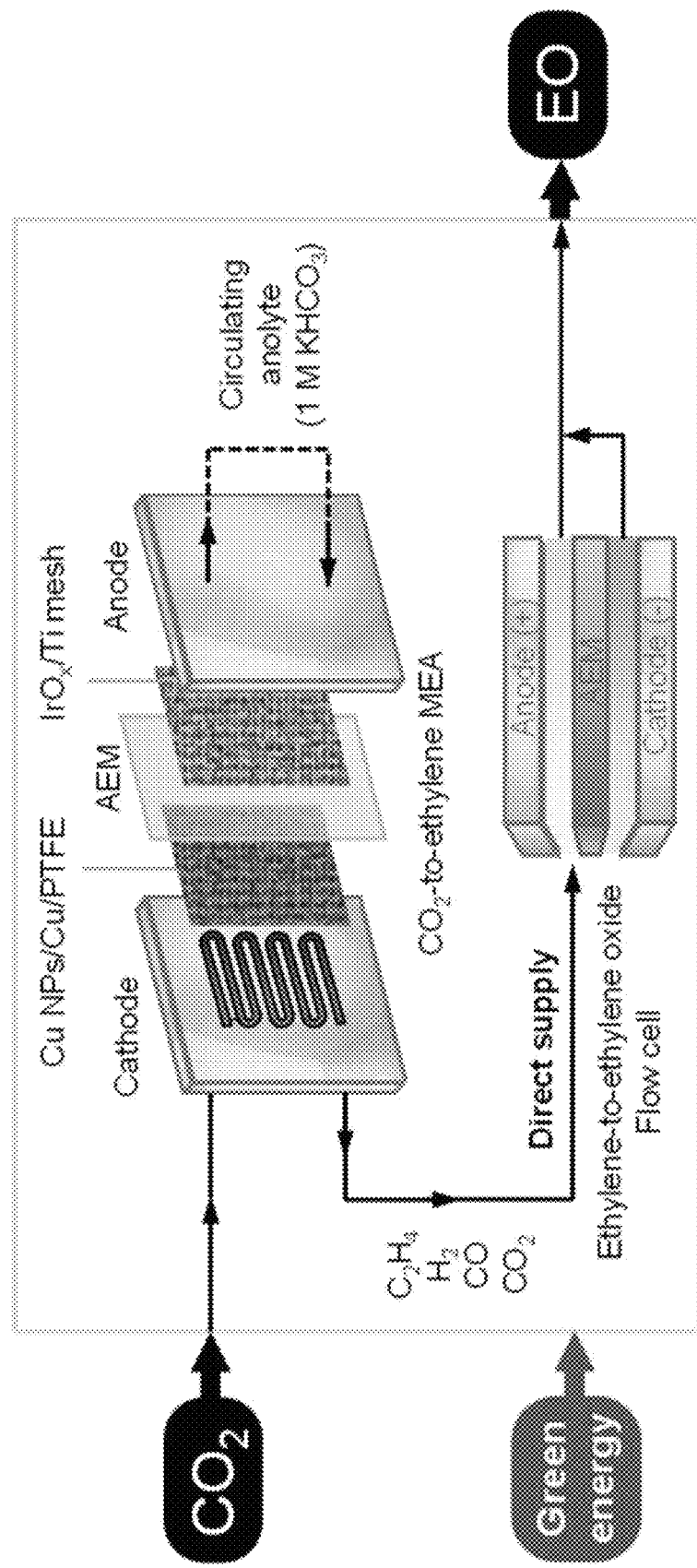
Figure 4D:
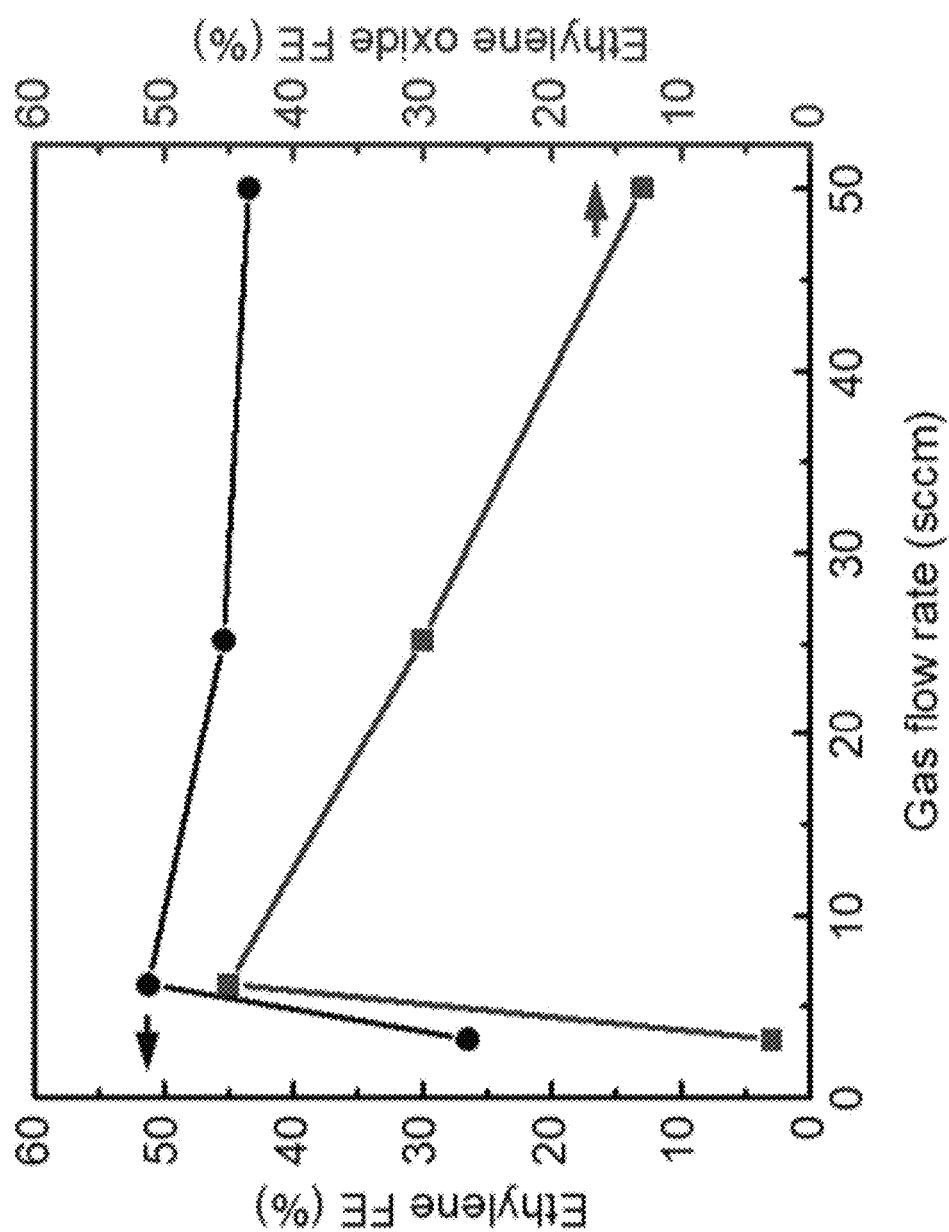

Finally, this work sought to develop an integrated system to perform the electrosynthesis of ethylene oxide from $CO_2$ (rather than ethylene) as the starting feedstock. This provides a route to directly use renewable electricity for recycling $CO_2$ into a valuable commodity chemical. In this integrated system, $CO_2$ reduction to ethylene is first performed using a membrane electrode assembly (MEA) in a gas diffusion configuration (FIG. 4C). The MEA comprises a copper nanoparticle/copper/polytetrafluoroethylene (Cu NPs/Cu/PTFE) cathode and an $IrO_x$/Ti mesh anode separated by an AEM, through which 0.1 M $KHCO_3$ anolyte was continuously circulated. The operating current density was kept at 240 mA/cm$^2$ and the ethylene Faradic efficiency is generally maintained at 43-52% (FIG. 4D). The flow rate of the output gas was measured using a flow meter at the cathode gas outlet, and directly sparged into the anolyte of the ethylene-to-ethylene oxide flow cell (operated at 300 mA/cm$^{-2}$) without further purification.

Figure 14B:
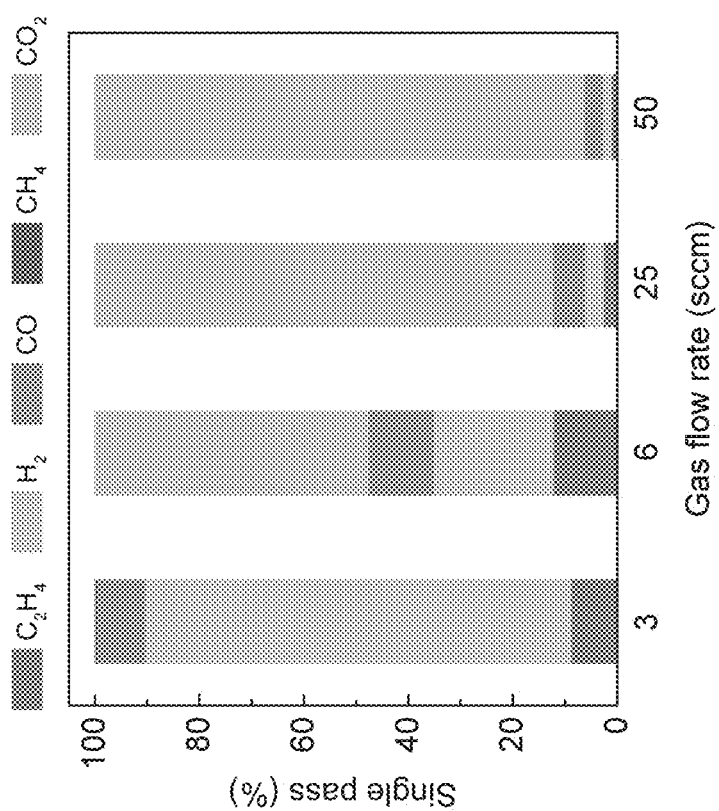
FIG. 14. (A) Faradaic efficiencies and (B) composition of the MEA outlet gas stream at different gas flow rates.
Figure 14A:
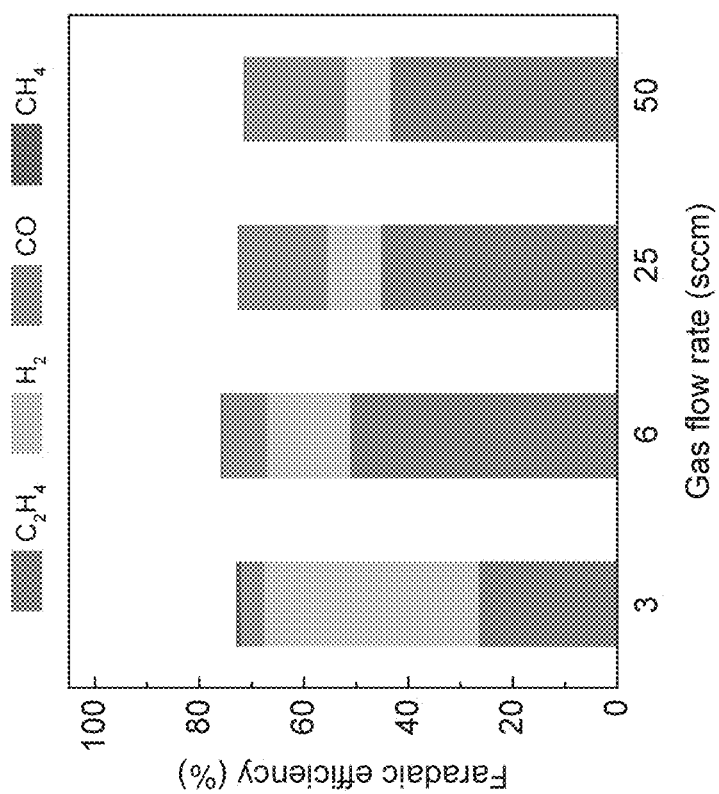

Through this method, this work achieves a Faradaic efficiency of 45% toward ethylene oxide under a gas flow rate of 6 sccm (FIG. 4D), despite the presence of other easily oxidizable gases such as $H_2$ and CO relative to ethylene (23% $H_2$, 12% CO and 12% ethylene, see FIG. 14). It is noted that the oxidation of these gases requires direct contact with the anode, whereas ethylene oxidation is mediated by the extended heterogeneous:homogeneous interface and thus occurs in the bulk electrolyte at a much higher rate. The Faradaic efficiency towards ethylene oxide is reduced at a higher gas flow rate due to lowered ethylene concentration in the MEA output stream (see FIG. 14). However, decreasing the flow rate even further (3 sccm) results in a lowered Faradaic efficiency towards ethylene in the MEA. This reduces the ethylene supply available for conversion in the flow cell, resulting in a drop in the Faradaic efficiency towards ethylene oxide. Thus, both concentration and molar quantity of ethylene in the MEA output stream are important determinants for the Faradaic efficiency toward ethylene oxide in the flow cell.

In conclusion, this work reports a strategy to produce ethylene oxide, with ethylene, renewable energy, and water as the raw inputs. An extended heterogeneous:homogeneous interface, using Cl$^-$ as a reservoir for positive charges from the anode, enables us to overcome the problems of over-oxidation and mass transport limitations, which enables a stable Faradaic efficiency of 71(±1) % toward ethylene oxide at a high current density of 300 mA/cm$^2$ for 100 h. This work achieved a Faradaic efficiency of 45% to ethylene oxide in an integrated system using ethylene generated from a $CO_2$-to-ethylene MEA. This demonstration shows the viability of an integrated system for complete $CO_2$-to-ethylene oxide conversion. Further improvements are expected by optimizing the ethylene Faradaic efficiency and single pass conversion in the MEA. In light of the energy-to-product efficiency and operating stability, this strategy is one platform to develop processes that utilize renewable electricity for the production of chemicals with the aim of a decarbonized chemicals industry.

INITIAL REFERENCES AND NOTES

1. "Energy use in industry," *Use of energy explained* (U.S. Energy Information Administration, 2019).
2. S. Chu, Y. Cui, N. Liu, The path towards sustainable energy. *Nat. Mater.* 16, 16 (2016).
3. Z. W. Seh et al., Combining theory and experiment in electrocatalysis: Insights into materials design. *Science* 355, eaad4998 (2017).
4. J. Zheng, S. Suh, Strategies to reduce the global carbon footprint of plastics. *Nat. Clim. Change.* 9, 374-378 (2019).
5. P. De Luna et al., What would it take for renewably powered electrosynthesis to displace petrochemical processes? *Science* 364, eaav3506 (2019).
6. M. Jouny, W. Luc, F. Jiao, General Techno-Economic Analysis of $CO_2$ Electrolysis Systems. *Ind. Eng. Chem. Res.* 57, 2165-2177 (2018).
7. C. Xia, Y. Xia, P. Zhu, L. Fan, H. Wang, Direct electrosynthesis of pure aqueous $H_2O_2$ solutions up to 20% by weight using a solid electrolyte. *Science* 366, 226-231 (2019).
8. R. F. Service, Renewable bonds. *Science* 365, 1236-1239 (2019).
9. S. Rebsdat, D. Mayer, in *Ullmann's Encyclopedia of Industrial Chemistry*. (2001).
10. "Ethylene," WP Report. (SRI Consulting., 2009).
11. "Ethylene oxide," WP Report. (SRI Consulting., 2009).
12. "Bio-Mono Ethylene Glycol (MEG) from renewable source—An India Glycols Limited case study," (International Council of Chemical Associations, 2017).
13. S. T. Wismann et al., Electrified methane reforming: A compact approach to greener industrial hydrogen production. *Science* 364, 756-759 (2019).
14. K. M. Van Geem, V. V. Galvita, G. B. Marin, Making chemicals with electricity. *Science* 364, 734-735 (2019).
15. D. Dudley, "Renewable Energy Costs Take Another Tumble, Making Fossil Fuels Look More Expensive Than Ever," (Forbes, 2019).

16. H. G. Cha, K.-S. Choi, Combined biomass valorization and hydrogen production in a photoelectrochemical cell. *Nat. Chem.* 7, 328 (2015).
17. N. Jiang, B. You, R. Boonstra, I. M. Terrero Rodriguez, Y. Sun, Integrating Electrocatalytic 5-Hydroxymethylfurfural Oxidation and Hydrogen Production via Co—P-Derived Electrocatalysts. *ACS Energy Lett.* 1, 386-390 (2016).
18. B. You, N. Jiang, X. Liu, Y. Sun, Simultaneous H2 Generation and Biomass Upgrading in Water by an Efficient Noble-Metal-Free Bifunctional Electrocatalyst. *Angew. Chem. Int. Ed.* 55, 9913-9917 (2016).
19. T. Li, Y. Cao, J. He, C. P. Berlinguette, Electrolytic CO2 Reduction in Tandem with Oxidative Organic Chemistry. *ACS Cent. Sci.* 3, 778-783 (2017).
20. R. S. Sherbo, R. S. Delima, V. A. Chiykowski, B. P. Macleod, C. P. Berlinguette, Complete electron economy by pairing electrolysis with hydrogenation. *Nat. Catal.* 1, 501-507 (2018).
21. J. Zheng et al., Hierarchical Porous NC@CuCo Nitride Nanosheet Networks: Highly Efficient Bifunctional Electrocatalyst for Overall Water Splitting and Selective Electrooxidation of Benzyl Alcohol. *Adv. Funct. Mater.* 27, 1704169 (2017).
22. D. Liu et al., Selective photoelectrochemical oxidation of glycerol to high value-added dihydroxyacetone. *Nat. Commun.* 10, 1779 (2019).
23. Y. Kwon, Y. Birdja, I. Spanos, P. Rodriguez, M. T. M. Koper, Highly Selective Electro-Oxidation of Glycerol to Dihydroxyacetone on Platinum in the Presence of Bismuth. *ACS Catal.* 2, 759-764 (2012).
24. C. Dai et al., Electrochemical production of lactic acid from glycerol oxidation catalyzed by AuPt nanoparticles. *J. Catal.* 356, 14-21 (2017).
25. A. Winiwarter et al., Towards an atomistic understanding of electrocatalytic partial hydrocarbon oxidation: propene on palladium. *Energy Environ. Sci.* 12, 1055-1067 (2019).
26. Y. Huang, X. Chong, C. Liu, Y. Liang, B. Zhang, Boosting Hydrogen Production by Anodic Oxidation of Primary Amines over a NiSe Nanorod Electrode. *Angew. Chem. Int. Ed.* 57, 13163-13166 (2018).
27. C. Huang, Y. Huang, C. Liu, Y. Yu, B. Zhang, Integrating Hydrogen Production with Aqueous Selective Semi-Dehydrogenation of Tetrahydroisoquinolines over a Ni2P Bifunctional Electrode. *Angew. Chem. Int. Ed.* 58, 12014-12017 (2019).
28. Y. Lum et al., Tuning OH binding energy enables selective electrochemical oxidation of ethylene to ethylene glycol. *Nature Catalysis* 3, 14-22 (2020).
29. M. Rafiee, K. C. Miles, S. S. Stahl, Electrocatalytic Alcohol Oxidation with TEMPO and Bicyclic Nitroxyl Derivatives: Driving Force Trumps Steric Effects. *J. Am. Chem. Soc.* 137, 14751-14757 (2015).
30. E. J. Horn et al., Scalable and sustainable electrochemical allylic C—H oxidation. *Nature* 533, 77 (2016).
31. M. Rafiee, F. Wang, D. P. Hruszkewycz, S. S. Stahl, N-Hydroxyphthalimide-Mediated Electrochemical Iodination of Methylarenes and Comparison to Electron-Transfer-Initiated C—H Functionalization. *J. Am. Chem. Soc.* 140, 22-25 (2018).
32. M. Eigen, K. Kustin, The Kinetics of Halogen Hydrolysis. *Journal of the American Chemical Society* 84, 1355-1361 (1962).
33. C. L. McCabe, J. C. Warner, The Kinetics of the Reaction between the Ethylene Halohydrins and Hydroxyl Ion in Water and Mixed Solvents1a. *Journal of the American Chemical Society* 70, 4031-4034 (1948).
34. "Market Analytics: Propylene Oxide—2018," *Markets & Profitability* (Nexant, Inc., 2018).
35. W. Luc, J. Rosen, F. Jiao, An Ir-based anode for a practical CO2 electrolyzer. *Catal. Today* 288, 79-84 (2017).

The following supplementary information is also provided and includes Materials and Methods, reference to FIGS. 5-14, additional References (1-5):

Materials and Methods

Preparation of Catalyst

The nanostructured palladium anode was deposited on a Ti mesh (100 mesh, Stanford Advanced Materials) using a solution of 2 mM potassium hexachloropalladate (IV) (99%, Sigma-Aldrich) in 0.5 M $H_2SO_4$ (99.999%, Sigma-Aldrich), with Pd foil as the counter and Ag/AgCl (3.0 M KCl) as the reference electrode. The potential of −1.0 V vs. Ag/AgCl was applied for a duration of 1000 s. The Pd anode was then rinsed with DI water and dried in a nitrogen stream.

The $IrO_2$/Ti anode was fabricated by etching the Ti mesh in boiling 6 M HCl (≥98%, Sigma-Aldrich) for 40 min, followed by dip-coating in a solution comprised of 2 mL HCl, 18 mL isopropanol, and 60 mg iridium (IV) oxide dihydrate (99.99%, Alfa Aesar) (1). The resultant catalyst was dried in a preheated oven at 100° C. for 10 min and calcined in air at 500° C. for 10 min. The procedure was repeated 10 times to achieve an $IrO_2$ loading of ~1 mg/cm².

The Cu NPs/Cu/PTFE cathode for the $CO_2$-to-ethylene membrane-electrode assembly (MEA) were fabricated by sputtering the commercially available Copper (Cu) target onto a PTFE substrate with an average pore size of 450 μm. A constant sputtering rate of 0.55 Å/sec was applied under 10-6 Torr until the ideal thickness of 150 nm was achieved. To increase the active catalytic surface area of the Cu/PTFE, a catalyst slurry composed of Cu NPs (25 nm average particle size, Sigma Aldrich®), polymeric binder (Aquivion® D-7925BS, Sigma Aldrich®), and methanol was spray-deposited layer-by-layer until the nominal catalyst loading of 1.25 mg/cm² was achieved. The weight ratio (wt %) between the polymeric binder and Cu NPs was 1:4. The resulting electrode was dried overnight under vacuum prior to electrochemical experiments.

Electrochemical Measurements

All olefin oxidation experiments were conducted in a flow-cell configuration consisting of the anode catalyst, anion exchange membrane (Fumasep FAB-PK-130) and Ni foam cathode (1.6 mm thickness, MTI Corporation). These were positioned and clamped together with polytetrafluoroethylene (PTFE) spacers to enable the introduction of liquid electrolyte into the anodic and cathodic chambers. The electrolyte was circulated through the cell at 10 ml/min using peristaltic pumps with a silicone Shore A50 tubing, during which ethylene or propylene gas (Gr 2.5, 99.5%, Linde Gas) was continuously sparged into the anolyte at a constant flow rate (15 sccm). For carbon-13 experiments, $^{13}C_2H_4$ (99%, Cambridge Isotope Laboratories, Inc) was used instead. Electrochemical measurements were carried out using an Autolab PGSTAT204 in a amperostatic mode and an Ag/AgCl reference electrode (3.0 M KCl). The reported current densities are based on the geometric electrode area (cm²).

For ethylene oxidation on the Pd anode, 1 M $NaClO_4$ electrolyte (98%, Sigma-Aldrich) was used. The organic mediators TEMPO (98%, Sigma-Aldrich) and NHPI (97%, Sigma-Aldrich) were used in conjunction with the same electrolyte and Pt foil anode (0.1 mm, Alfa Aesar).

The liquid products were analyzed using HPLC (Thermo Scientific Dionex UltiMate 3000) and $^1$H NMR spectroscopy (600 MHZ Agilent DD2 NMR Spectrometer) using water 400 suppression techniques. For $^{13}$C NMR spectroscopy, the products were analyzed continuously for 4 h to accumulate sufficient signal and proton decoupling techniques were employed to prevent $^1$H protons from splitting the $^{13}$C nuclei. All reported Faradaic efficiencies were averaged from at least three different runs.

The electrochemical performance testing of the MEA electrolyser was performed by using an electrochemical test station, equipped with a commercial software, current booster and potentiostat, mass flow controller, peristaltic pump with silicon tubing, and humidified. The MEA electrolyser used was commercially available and composed of three main constituents: as-prepared cathode electrode, anode electrode (Ti—IrO$_2$), and anion exchange membrane (AEM, Dioxide Materials, Classic Sustainion® 37-50). The cathode electrode was mounted onto the metallic surface of the cathode flow-field via a frame made of Cu tape for electrical connection between the electrode and flow-field, while the Ti—IrO$^2$ mesh was mounted onto the anode flow field, and the anode and cathode flow fields were separated by the AEM. The commercial AEM was activated for at least 24 hours earlier prior to being used for performance testing. The electrolyser was then assembled by applying an equal compression torque to the each of four bolts. After the assembly, 0.1 M KHCO$_3$ was circulate through the anode side while humidified CO$_2$ with the flow rate of test-of-interest flow rates (3 sccm, 6 sccm, 25 sccm, and 50 sccm) was supplied to the cathode side. Upon completion of 3-min of initial reactant and anolyte supply, a constant current density of −240 mA/cm$^2$ was applied to the working electrode, and the electrolyser was operated under these initially set conditions throughout the course of the experiments.

Faradaic efficiency (FE) calculation towards ethylene was made according to the following expression:

$$\text{Faradaic Efficiency} = \frac{F n_a V_{gas} c_a}{i_{overall} V_m}$$

where F is the Faraday constant, $n_a$ is the number of electron transfer required for 1 mol ethylene production, $V_{gas}$ stands for the flow rate of CO$_2$, $V_{gas}$ is the volume of the gas sample collected for injection into the gas chromatography (p.p.m.), $c_a$ is the concentration of ethylene measured by via GC, $i_{overall}$ is the overall current measured, and $V_m$ is the unit molar volume of CO$_2$.

Materials Characterization

The morphologies of the electrodes were investigated through SEM using a Hitachi S-5200 apparatus at a 15 kV beam voltage and TEM on a Hitachi HF-3300 equipped with a Bruker energy dispersive x-ray spectroscopy detector at an acceleration voltage of 300 kV. The XPS measurements were conducted with a Thermofisher Scientific K-Alpha with a monochromated Al Kα X-ray source. XRD measurements were performed on a Rigaku MiniFlex 600.

Iodometric Titration

Iodometric titration of the anolyte was conducted by first adding an excess of 10% KI solution to react with the unreacted chlorine/hypochlorite species and form iodine, followed by starch solution to form a dark blue starch-iodine complex. This was then titrated with 1 M NaS$_2$O$_3$ solution until the anolyte turned clear again, and the amount of NaS$_2$O$_3$ was recorded and used to determine the Faradaic efficiency of unreacted chlorine/hypochlorite species.

Additional Comments

Techno-Economic Analysis

To determine the economic potential of renewable electricity powered production of ethylene oxide from ethylene, this work conducted a techno-economic analysis (TEA) based on a modified model from our previous work (2). Fig. S1 shows the model used to calculate the plant-gate levelized cost of ethylene oxide production (US$ per ton of ethylene oxide).

Below is the list of assumptions made for the calculations.
1. The production capacity of the plant is 1 ton of ethylene oxide per day.
2. The total catalyst and membrane cost is 5% of the total electrolyzer cost.
3. The total cost of the electrolyzer is $10,000 per m$^2$.
4. The price of electricity, unless otherwise stated, is 10 ¢/kWh, which is the upper bound to
the current cost of renewable electricity.
5. The separation cost comprises 2 components, gas stripping costs for separation of ethylene oxide (3) and an ethylene gas separation and recycle system. Their combined cost is assumed to be 20% of the electricity cost.
6. Other operation costs are assumed to be 10% of the electricity cost.
7. The capacity factor, i.e., the fraction of time the plant is expected to be operational on any given day, is assumed to be 0.8, which means the plant will be operational 19.2 hours a day.
8. The faradaic efficiency to ethylene oxide is 70%, the cell operating voltage is 3.0 V and the total operating current density is 300 mA/cm$^2$.
9. The prices of ethylene and ethylene oxide are assumed to be $900 per ton and $1400 per ton respectively (4).
10. The price of hydrogen is $1,900 per ton (5). The faradaic efficiency for hydrogen generation is assumed to be 100%.

TEA Cost Components

To calculate the cost components shown in Fig. S1, the following equations are used:

$$\text{Catalyst and membrane cost}(\$/\text{ton}) = \frac{\text{Total cost of electrolyzer}(\$) \times 5\%}{\text{Catalyst lifetime (year)} \times 365(\text{day}/\text{year}) \times \text{Production of product (ton}/\text{day})}$$

$$\text{Electrolyzer cost }(\$/\text{ton}) = \frac{\text{Total cost of eletrolyzer}(\$) \times \text{Capital recovery factor}}{\text{Capacity factor} \times 365(\text{day}/\text{year}) \times \text{Production of product (ton}/\text{day})}$$

$$\text{Total cost of electrolyzer }(\$) = \text{Total surface area needed }(m^2) \times \text{Price per } m^2 \ (\$/m^2)$$

-continued $$\text{Total surface area needed} (m^2) = \frac{\text{Total current needed } (A)}{\text{Current density } (A/m^2)}$$

Total current needed $(A) =$ $$\frac{\text{Plant capacity (ton/day)} \times \text{No. of } e^- \text{transferred in reaction} \times 96485 (C/\text{mol})}{\text{Product molecular weight (ton/mol)} \times 24 (\text{hour/day}) \times 3600 (s/\text{hour}) \times \text{Faradaic Efficiency (\%)}}$$

$$\text{Capital recovery factor} = \frac{\text{Discount rate} \times (1 + \text{Discount rate})^{Lifetime}}{(1 + \text{Discount rate})^{Lifetime} - 1}$$

$$\text{Electricity cost}(\$/\text{ton}) = \frac{\text{Power consumed (kW)} \times 24(\text{hour}/\text{day}) \times \text{Electricity cost}(\$/\text{kwh})}{\text{Plant capacity (ton/day)}}$$

$$\text{Power consumed (kW)} = \frac{\text{Total current needed } (A) \times \text{Cell voltage } (V)}{1000(W/\text{kW})}$$

Maintenance cost $(\$/\text{ton}) =$

Maintenance frequency × Maintenance factor (% of Capital cost) × Total capital cost ($/ton)

Balance of plant ($/ton) = Balance of plant factor (%) × Capital cost ($/ton)

Installation cost ($/ton) = Lang factor (%) × Capital cost ($/ton)

TABLE 2

Iodometric titration of the anolyte solution

| Current density (mA/cm$^2$) | Amount of Na$_2$S$_2$O$_3$ added (mmol) | Amount of unreacted chlorine/ hypochlorite species (mmol) | Faradaic efficiency loss due to unreacted hypochlorite (%) |
|---|---|---|---|
| 300 | 2.8 | 1.4 | 25 |

SUPPLEMENTARY REFERENCES

1. W. Luc, J. Rosen, F. Jiao, An Ir-based anode for a practical CO$_2$ electrolyzer. *Catal. Today* 288, 79-84 (2017).
2. P. De Luna et al., What would it take for renewably powered electrosynthesis to displace petrochemical processes? *Science* 364, eaav3506 (2019).
3. "Ethylene Oxide Production by Nippon Shokubai Process," *PEP Review* 2010-12 (IHS Markit, 2010).
4. "Ethylene oxide (EO) Prices and Information," (ICIS Ltd., 2011).
5. O. S. Bushuyev et al., What Should We Make with CO2 and How Can We Make It? *Joule* 2, 825-832 (2018).
6. Electrolysis System and Method for Electrochemical Ethylene Oxide Production, United States Patent Application 20190032228.

The invention claimed is:

1. An electrocatalyst for selective anodic oxidation of an olefin reactant to produce ethylene chlorohydrin in a halide ion based electrolyte, the electrocatalyst comprising iridium oxide on a titanium substrate, where the titanium substrate is in the form of a titanium mesh.

2. The electrocatalyst of claim 1, wherein the iridium oxide is provided as nanoparticles on the titanium substrate.

3. The electrocatalyst of claim 1, wherein the iridium oxide is provided as particles on the titanium substrate.

4. The electrocatalyst of claim 1, wherein the titanium mesh comprises a network of filaments defining openings, and the iridium oxide is deposited on the filaments and also forms an iridium oxide web extending across the openings.

5. The electrocatalyst of claim 1, wherein the iridium oxide is provided at a loading of at least 1 mg/cm$^2$ on the titanium substrate.

6. The electrocatalyst of claim 1, wherein the iridium oxide is provided as a dip-coated layer on an etched surface of the titanium substrate.

7. An electrochemical process for producing oxirane from olefin reactants, comprising:
    contacting a halide based electrolyte with an anode and a cathode respectively located in an anodic compartment and a cathodic compartment;
    supplying olefin reactants into the electrolyte in the anodic compartment, such that the anode generates ethylene chlorohydrin;
    withdrawing a loaded anodic solution comprising ethylene halohydrin from the anodic compartment, and a loaded cathodic solution comprising OH$^-$ ions from the cathodic compartment;
    mixing at least a portion of the loaded anodic solution with at least a portion of the loaded cathodic solution under conditions to react ethylene halohydrin with OH— to produce oxirane; and
    wherein the anode comprises an electrocatalyst as defined in claim 1.

8. The process of claim 7, wherein the olefin reactants are ethylene.

9. The process of claim 7, wherein the halide based electrolyte is an aqueous KCl solution and the ethylene halohydrin comprises ethylene chlorohydrin.

10. The process of claim 7, wherein the halide based electrolyte is provided at a concentration of about 1.5 to 2.5 M.

11. The process of claim 7, wherein the electrocatalyst is fabricated by etching the titanium substrate followed by coating the etched titanium substrate in a coating solution comprising a dihydrate of the iridium oxide.

12. The process of claim 11, wherein the etching is performed in a boiling HCl solution; wherein the boiling HCl solution is at 5 M to 7 M and the etching is performed for at least 30 or 40 minutes; wherein the coating comprises dip-coating; wherein the coating solution comprising the dihydrate of the metal oxide catalyst further comprises HCl and an alcohol; wherein the coating solution comprises iridium (IV) oxide dihydrate as the dihydrate of the iridium oxide; wherein the process further comprises drying the wet electrocatalyst, optionally in an oven that is at 50° C. to 150° C. and optionally for at least 10 minutes, and calcining the dried electrocatalyst, optionally at a calcining temperature of at least 500° C. and optionally for at least 10 minutes.

13. The process of claim 7, wherein the iridium catalyst is provided at a loading of at least 1 mg/cm$^2$ on the titanium substrate.

14. The process of claim 7, wherein the electrolyte is continuously circulated through the anodic and cathodic compartments, and the olefin is continuously sparged into the anodic compartment.

15. The process of claim 7, wherein the loaded anodic solution and the loaded cathodic solution are merged post electrolysis.

16. The process of claim 7, wherein the anodic compartment and the cathodic compartment are separated by an ion exchange membrane.

17. The process of claim 7, wherein the electrochemical process is operated at a current density 100 to 300 mA/cm$^2$ or greater.

18. The process of claim 7, wherein some or all of the olefin reactants are generated by a $CO_2$-to-ethylene membrane electrode assembly.

19. An electrochemical process for producing oxiranes from olefin reactants, comprising:
 contacting a halide based electrolyte with an anode and a cathode respectively located in an anodic compartment and a cathodic compartment;
 supplying olefin reactants into the electrolyte in the anodic compartment, such that the olefin reactants contact the anode;
 wherein the anode comprises an electrocatalyst that defines an extended heterogenous:homogenous interface with halide ions acting as a reservoir for positive charges, thereby storing and redistributing positive charges to promote selective generation of ethylene halohydrins; and
 converting the ethylene halohydrins into oxiranes; and
 wherein the anode comprises an electrocatalyst as defined in claim 1.

* * * * *